US006548062B2

(12) United States Patent
Buchkovich et al.

(10) Patent No.: US 6,548,062 B2
(45) Date of Patent: Apr. 15, 2003

(54) METHOD OF TREATING CANCER WITH ANTI-NEUROTROPHIN AGENTS

(75) Inventors: Karen J. Buchkovich, Audubon, PA (US); Craig A. Dionne, Downingtown, PA (US); Sheila J. Miknyoczki, Easton, PA (US); Bruce A. Ruggeri, Paoli, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 09/793,850

(22) Filed: Feb. 27, 2001

(65) Prior Publication Data

US 2001/0046959 A1 Nov. 29, 2001

Related U.S. Application Data

(60) Provisional application No. 60/185,943, filed on Feb. 29, 2000.

(51) Int. Cl.$^7$ ............................................. A61K 39/395
(52) U.S. Cl. ............................... 424/133.1; 424/130.1; 424/138.1; 424/139.1
(58) Field of Search ...................... 424/130.1, 138.1, 424/139.1, 133.1

(56) References Cited

U.S. PATENT DOCUMENTS

5,844,092 A 12/1998 Presta et al.

FOREIGN PATENT DOCUMENTS

| WO | 93/09798 | 5/1993 |
| WO | 94/06935 | 3/1994 |
| WO | 26363 | * 10/1995 |

OTHER PUBLICATIONS

Johnson et al, Cancer Treatment Reviews vol. 2 p. 1–31 (1975).*
Ro Long–Sun et al., Pain, 1999, 79(2–3), 265–274; {Abstract}, Database BIOSIS 'Online!, Database accession No. PREV199900141371 XP002175589.
Woolf, Clifford J., Philosophical Transactions of the Royal Society of London B Biological, 1996, 351(1338), 441–448; {Abstract}, Database BIOSIS 'Online!, Database accession No. PREV199698828031 XP0021175590.
Chang H. et al., Proceedings of the American Association For Cancer Research Annual, 2000, 41, 812; {Abstract}, XP001015650.
Pahlman, S; Hoehnor, J. C. Mol. Med. Today, 1996, 432–438.
Chang, H. et al., Proc. Am. Assoc. Cancer Res., 2000, 41:#5157,812.
Frederick, W. et al., Proc. Am. Assoc. Cancer Res., 2000, 41:#5534,871.
Ohta et al., J. Pathol., 1997, 181, 405.
Ruggeri, B. A. et al., Current Medicinal Chemistry, 1999, 6, 845–857.
Delsite, R.; Djakiew, D., Journal of Andrology, 1996, 17(5), 481.
Djakiew, D. et al., Biology of Reproduction, 1994, 51, 214–221.
Miralles, F. et al., Journal of Endocrinology, 1998, 156, 431–439.
Pflug, B.; Djakiew, D., Molecular Carcinogenesis, 1998, 23, 106–114.
Kramer, K. et al., European Journal of Cancer, 1997, 33(12), 2090–2091.
Djakiew, D. et al., The Underlying Molecular, Cellular, and Immunological Factors in Cancer and Aging; S.S. Yang and H. R. Warner, Eds; Plenum Press: New York, 1993 p. 185–202.
Angeles, T. S. et al., Archives of Biochemistry and Biophysics, 1998, 349(2), 267–274.
Klein et al., Cell, 1990, 61, 647.
Tsoulfas et al., Neuron, 1993, 10, 975–990.
Dionne et al., Clin. Cancer Res., 1998, 4, 1887–1898.
Miknyoczki et al., Clin. Cancer Res., 1999, 5, 2205–2212.
LeSauteur, L. et al., Nature Biotechnology, 1996, 14, 1120.
Li, Y. et al, Proc. Natl. Acad. Sci., 1998, 95, 10884–10889.
Maroney A. C. et al., Journal of Neurochemistry, 1995, 540.
Kaneko, M. et al., J. Med. Chem., 1997, 40, 1863–1869.
George, D. J. et al., The Prostate, 1998, 36, 172–180.
Pflug, B. R. et al., Cancer Research, 1992, 52, 5403–5406.
Passaniti, A. et al., Int. J. Cancer, 1992, 51, 318–324.
Djakiew, D. et al., Cancer Research, 1991, 51, 3304–3310.
Miknyoczki, S. J. et al., Critical Reviews™ in Oncogenesis, 1996, 7(1&2), 89–100.
Pflug, B. R. et al., Endocrinology, 1995, 136(1), 262–268.
Camoratto, A. M. et al., Int. J. Cancer, 1997, 72, 673–679.
George, D. J. et al., Cancer Research, 1999, 59, 2395–2401.
Miknyoczki, S. J. et al., Int. J. Cancer, 1999, 81, 417–427.
Miknyoczki, S. J. et al., Clinical Cancer Research, 1999, 5, 2205–2212.
Dionne, C. A. et al., Clinical Cancer Research, 1998, 4, 1887–1898.
Valenzuela, D. M. et al., Neuron, 1993, 10, 963–974.
Eide, F. F. et al., The Journal of Neuroscience, 1996, 16(10), 3123–3129.
Oikawa, T. et al., International Journal of Pancreatology, 1995, 18(1), 15–23.

* cited by examiner

Primary Examiner—Sheela Huff
(74) Attorney, Agent, or Firm—Woodcock Washburn LLP

(57) ABSTRACT

A method of treating or preventing cancer by administering to a mammal a therapeutically effective amount of at least one anti-neurotrophin agent is described. The anti-neurotrophin agent is preferably an anti-neurotrophin antibody, an antisense molecule directed to a neurotrophin, a small organic molecule which binds a neurotrophin, or a dominant-negative mutation of a trk receptor that binds a neurotrophin. This method is particularly preferred for the treatment of prostate or pancreatic cancer. The anti-neurotrophic agents neutralize NGF, BDNF, NT-3, NT-4/5, NT-6 or NT-7 and include humanized antibodies as well as fragments thereof.

15 Claims, No Drawings

METHOD OF TREATING CANCER WITH ANTI-NEUROTROPHIN AGENTS

CROSS REFERENCE TO RELATED APPLICATIONS

This application claims the benefit under 35 U.S.C. §119 (e) of U.S. Application No. 60/185,943 filed Feb. 29, 2000.

FIELD OF THE INVENTION

The present invention relates to the field of oncology and is directed to a method for treating or preventing cancer, particularly prostate and pancreatic cancers. The present invention also pertains to the area of neurotrophins and the use of anti-neurotrophin agents such as, for example, antibodies, in treating or preventing cancer and/or pain.

BACKGROUND OF THE INVENTION

Neurotrophins (NTs) are a subfamily of specific neurotrophic factors including four well known structurally and functionally related proteins: nerve growth factor (NGF), brain-derived neurotrophic factor (BDNF), neurotrophin-3 (NT-3), neurotrophin-4/5 (NT-4/5). Recently, two additional NTs, neurotrophin-6 (NT-6) and neurotrophin-7 (NT-7), have been discovered. The neurotrophins bind to and activate specific cell surface membrane receptors which have tyrosine kinase activity. These receptors are known as trk receptors and are classified according to the three subtypes trkA, trkB, and trkC. Each trk receptor subtype binds preferentially to one or more NTs (NGF to trkA, BDNF and NT-4/5 to trkB, and NT-3 to trk C). NT cross reactivity, however, is known to occur between receptor subtypes. Activation of trk receptors by NTs results in receptor oligomerization and tyrosine phosphorylation of specific intracellular substrates. In addition to the trk receptors, a second type of cell surface membrane receptor is known to bind NTs. This receptor is the low-affinity nerve growth receptor $p75^{NTR}$ (p75) which is believed to be involved in modulation of NT affinity and/or availability for binding to higher affinity trk receptors. A specific physiological role for receptor p75, however, remains in debate.

It is widely recognized that NTs play an essential role in growth, differentiation, and survival of central and peripheral nervous system cells. There is recent evidence, however, that NTs also contribute to tumor biology outside the nervous system. Neurotrophins and their receptor subtypes have been implicated in various cancers including prostate, breast, thyroid, colon, and lung carcinomas, as well as malignant melanomas, pancreatic carcinoids, and glioblastomas. Specifically, aberrant expression of trk receptors A, B, and C have been found in pancreatic ductal adenocarcinoma (PDAC), and NTs can influence the invasiveness of this tumor type (Miknyoczki, et al., *Int. J. Cancer,* 1999, 81, 417). In addition, NGF has been correlated with perineural invasion and pain that is associated with PDAC (Zhu, et al., *J. Clin. Oncol.,* 1999, 17, 2419). TrkA is also known to be expressed in prostatic epithelial tissue, and the corresponding neurotrophin NGF has been implicated in the stimulation of prostate cancer growth. Immunoreactivity for NGF has been demonstrated in human prostatic carcinomas (De Schryver-Kecskemeti et al, *Arch. Pathol.,* 1987, 111, 833) and tumor-derived cell lines (MacGrogan et al., *J. Neurochem.,* 1992, 59, 1381) suggesting a possible mitogenic or survival role for NGF in this cancer. Further, prostatic carcinoma cells have been shown to be chemotactic (Djakiew, et al., *Cancer. Res.,* 1993, 53, 1416) and invasive (Geldof, et al., *J. Cancer Res. Clin. Oncol.,* 1997, 123, 107) in response to NGF in vitro.

Trks have been shown to play a role in both prostatic cancer (Delsite et al., *J. Androl.,* 1996, 17, 481, Pflug et al, *Endocrinology,* 1995, 136, 262, Pflug et al., *Cancer Res.,* 1992, 52, 5403, Djakiew et al., *Cancer Res.,* 1991, 51, 3304, Passaniti et al., *Int. J. Cancer,* 1992, 51, 318, MacGrogan et al., *J. Neurochem.,* 1992, 59, 1381, Geldof et al., *J. Cancer Res. Clin. Oncol.* 1997, 123, 107, Pflug et al., *Mol. Carcin.,* 1998, 12, 106, and George et al., *The Prostrate,* 1998, 36, 172) and pancreatic cancer (Oikawa, et al., *Int. J. Pancreat.,* 1995, 18, 15, Ohta et al., *J. Pathol.,* 1997, 181, 405, Miralles et al., *J. Endocrinology,* 1998, 156, 431, and Miknyoczki et al., *Crit. Rev. Oncogenesis,* 1996, 7, 89).

Due to the possible role of trk activity in the development and progression of certain cancers, selective disruption of NT-trk axes has been targeted as a possible therapeutic means. Specifically, small molecules have been developed and tested which show ability to inhibit trk receptors (Ruggeri, et al., *Current Medicinal Chemistry,* 1999, 6, 845). The glycosylated indolocarbazole alkaloids K-252a and K-252b are known to inhibit the biological actions of NGF and other neurotrophins. K-252a has been reported to specifically inhibit the autophosphorylation of trkA as well as trkB and trkC and other related neurotrophin receptors at low nanomolar concentrations (Hashimoto, *Cell Biol.,* 1988, 107, 1531; Berg, et al., *J. Biol. Chem.,* 1992, 267, 13; Tarpley, et al., *Oncogene,* 1992, 7, 371; Ohmichi, et al, *Biochemistry,* 1992, 31, 4034; Muroya, et al., *Biochim. Biophys. Acta.,* 1992, 1135, 353; and Nye, et al., *Mol. Biol. Cell,* 1992, 3, 677.) By modification of the sugar moiety of K-252a, two additional potent trk inhibitors have been developed. Specifically, CEP-751, a hydroxymethyl derivative of K-252a, has been found to be a potent inhibitor of trkA ($IC_{50}$ of 3 nM in an ELISA), trkB, and trkC. A dipeptide derivative, CEP-2563, was also synthesized which showed similar activity and improved water solubility. Another related compound, CEP-701, was also found to have good trkA inhibitory activity showing an $IC_{50}$ of 4 nM. Both CEP-751 and CEP-701 have been shown to significantly inhibit human and rat prostatic carcinomas in pre-clinical models (Dionne, et al., *Clin. Cancer Res.,* 1998, 4, 1887 and George, et al., *Cancer Research,* 1999, 59, 2395). CEP-751 has also been shown to display anti-tumor activity in neuroblastoma and medulloblastoma xenografts (Evans, et al., *Clin. Cancer Res.,* 1999, 5, 3594), as well as ovarian cancer and melanoma models. Further, significant anti-tumor activity by CEP-701 in preclinical xenograft models of human pancreatic ductal adenocarcinoma has also been shown (Miknyoczki, et al., *Clin. Cancer Res.,* 1999, 5, 2205). CEP-701 is currently undergoing human clinical trials.

Although these small molecule trk inhibitors can be used as tools for treating prostate, pancreatic, and other cancers, it is difficult to develop small molecules with specificity for a particular target molecule. One of the main concerns in general for small molecules is non-specificity for target receptors or receptor pathways, leading to undesirable activation or inactivation of other receptors and possible toxicity. For instance, K-252a has been shown to have multiple biochemical properties including neurotrophic activity in combination with trk and protein kinase C inhibiting activities (Kaneko, et al, *J. Med. Chem.,* 1997, 40, 1863). Thus, therapeutic agents with high specificity for biological targets which are involved in trk receptor activity are desirable as potential drug candidates for the treatment of prostate, pancreatic, and other cancers. To this end, antibodies directed to a particular trk receptor have been shown to be less desirable than small molecules (LeSauteur et al., *Nature Biotech.,* 1996, 14, 1120). The present invention provides a method for treating trk receptor-mediated cancers, such as, for example, pancreatic or prostrate cancer, by administering at least one neutralizing neurotrophin antibody to a mammal. The antibody treatment provides much desired specificity that small molecules may indeed not offer.

SUMMARY OF THE INVENTION

The present invention is directed to a method of treating or preventing cancer comprising administering to a mammal a therapeutically effective amount of at least one anti-neurotrophin agent. The anti-neurotrophin agent is preferably either an anti-neurotrophin antibody, an antisense molecule directed to a neurotrophin, a small organic molecule which binds a neurotrophin, and a dominant-negative mutation of a trk receptor that binds a neurotrophin. This method is particularly preferred for the treatment of prostate or pancreatic cancer. Anti-neurotrophin agents include those directed to NGF, BDNF, NT-3, and NT-4/5 and include humanized antibodies as well as fragments thereof. In a preferred embodiment, the method of treating or preventing cancer involves delivery of a therapeutically effective amount of at least one of the following neutralizing neurotrophin antibodies, NGF, BDNF, NT-3, and NT-4/5 to prostatic or pancreatic tumors.

Another aspect of the invention is directed to a method of reducing prostatic or pancreatic tumor volume comprising contacting the tumor with at least one anti-neurotrophin agent.

A further aspect of the invention involves a method of reducing prostatic or pancreatic tumor growth rate comprising contacting the tumor with at least one anti-neurotrophin agent.

Another aspect of the invention is directed to a method of reducing pain comprising administering to a mammal at least one anti-neurotrophin agent.

DESCRIPTION OF PREFERRED EMBODIMENTS

The method of the present invention is directed to the treatment and/or prevention of cancer in a mammal by administering to the mammal a therapeutically effective amount of at least one anti-neurotrophin agent. The anti-neurotrophin agent is preferably either an anti-neurotrophin antibody, an antisense molecule directed to a neurotrophin, a small organic molecule which binds a neurotrophin, and a dominant-negative mutation of a trk receptor that binds a neurotrophin. The anti-neurotrophin agents bind with high specificity to neurotrophins, thus leading to inhibition of trk receptors by neutralization of activating neurotrophin ligands.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the phrase "anti-neurotrophin agent" is meant to refer to any molecule that prevents the synthesis of or reduces the amount of synthesis of a neurotrophin or any molecule that inhibits or reduces the bioactivity of a neurotrophin. Preferred examples of anti-neurotrophin agents include, but are not limited to, an anti-neurotrophin antibody, an antisense molecule directed to a neurotrophin, a small organic molecule which binds a neurotrophin, and a dominant-negative mutation of a trk receptor that binds a neurotrophin.

As used herein, the term "cancer" is meant to refer to a persistent neoplasm of any tissue in a biological organism. The neoplasm is characterized as generally malignant or likely to become malignant, potentially invasive, or likely to metastasize to new sites. Preferred cancers of the present invention include are those that are associated with expression of neurotrophin receptors and neurotrophins including, but not limited to, prostate and pancreatic cancer.

As used herein, the term "tumor" is meant to refer to a growth arising from existing tissue, growing at an abnormal rate compared with the tissue it arose from, and serving no normal physiological function. The growth may or may not be malignant, but is often associated with, or indicative of, a cancerous or pre-cancerous state.

As used herein, the term "mammal" is meant to refer to either human or non-human living organisms that are afflicted with cancer, previously afflicted with cancer, or predisposed to cancer.

As used herein, the phrase "therapeutically effective amount" is meant to refer to an amount of therapeutic or prophylactic anti-neurotrophin agent, such as a neurotrophin antibody, that would be appropriate for an embodiment of the present invention, that will elicit the desired therapeutic or prophylactic effect or response when administered to in accordance with the desired treatment regimen.

As used herein, the term "antibody" is meant to refer to complete, intact antibodies, as well as F(ab) fragments and F(ab)$_2$ fragments thereof. Complete, intact antibodies include monoclonal antibodies such as murine monoclonal antibodies, polyclonal antibodies, chimeric antibodies, humanized antibodies, and derivatives of all of the aforementioned.

As used herein, the term "neurotrophin" or "NT" is meant to refer to any native or non-native neurotrophins including, but not limited to, NGF, BDNF, NT-3, NT-4/5, NT-6, and NT-7, and their functional derivatives or equivalents, whether purified from a native source, prepared by methods of recombinant DNA technology, or chemical synthesis, or any combination of these or other methods.

As used herein, the term "neutralizing" generally means rendering ineffective and, when used to describe an antibody, further means an antibody that renders ineffective the molecule to which it binds. In preferred embodiments of the invention, a "neutralizing" antibody binds to a particular ligand and prevents or interferes with binding of the ligand to its receptor.

As used herein, the term "contacting" means bringing together, either directly or indirectly, one or more molecules with another, thereby facilitating intermolecular interactions. Contacting may occur in vitro, ex vivo or in vivo.

As used herein, the term "neurotrophin receptor" is meant to refer to a receptor which binds a neurotrophin ligand. In preferred embodiments, the neurotrophin receptor is a member of the tyrosine kinase family of receptors, generally referred to as the "trk" receptors or "trks", which are expressed on cellular surfaces. The trk family includes, but is not limited to, trkA, trkB; and trkC. In other embodiments, the neurotrophin receptor is p75$^{NTR}$, also called p75 or low-affinity nerve growth factor receptor. These receptors may be from any animal species (e.g. human, murine, rabbit, porcine, equine, etc.), and include full length receptors, their truncated and variant forms, such as those arising by alternate splicing and/or insertion, and naturally-occurring allelic variants, as well as functional derivatives of such receptors.

In a preferred embodiment, the present invention is directed to a method of treating or preventing prostate or pancreatic cancers. Other neoplastic disease states, which can be characterized by expression of neurotrophin receptors such as trk receptors, may be treatable or preventable according to the present method. Neoplasms which express neurotrophin receptors include, but are not limited to, cancers associated with breast, thyroid, colon, lung, ovary, skin, muscle, kidney, reproductive organs, blood, immune system tissues (e.g. spleen, thymus, and bone marrow), and brain and peripheral nervous system tissues.

In other preferred embodiments, non-malignant tumors, pre-cancerous lesions, pre-cancerous tumors, or other pre-cancerous states which are associated with expression of neurotrophin receptors or associated with the aforementioned neoplastic disease states can also be treated or prevented according to the methods of the present invention. Such treatment would contribute to the prevention of cancer in patients with clinical signs of imminent cancer or a predisposition for cancer.

Preferred mammals of the present invention are human with susceptibility to or clinical diagnosis of prostate or pancreatic cancer. Naturally, non-human mammals afflicted with prostate or pancreatic cancer also fall within the scope of the present invention. Furthermore, both human and non-humans afflicted with the neoplasia listed hereinabove other than prostate and pancreatic cancers are included in the present invention. Mammals also include humans or non-humans who are predisposed to becoming afflicted with cancer. Examples include humans exposed to known carcinogens or male humans of an age for risk of developing prostate cancer. Also included are patients with a family history of cancer or who are genetically predisposed toward developing certain types of cancers.

In some embodiments of the invention, the anti-neurotrophin agent is an antisense molecule directed to a neurotrophin. Nucleotide sequences of the neurotrophins are as follows: NGF (Borsani et al., *Nuc. Acids Res.,* 1990, 18, 4020; Accession Number NM 002506), BDNF (Maisonpierre et al., *Genomics,* 1991, 10, 558; Accession Number M 61181), NT-3 (Jones et al., *Proc. Natl. Acad. Sci. USA,* 1990, 87, 8060; Accession Number M 37763; and Maisonpierre et al., Genomics, 1991, 10, 558; Accession Number M 61180), NT-4 (Ip et al., *Proc. Natl. Acad. Sci. USA,* 1992, 89, 3060; Accession Number M 86528), and NT-5 (Ip et al., *Proc. Natl. Acad. Sci. USA,* 1992, 89, 3060 and Berkemeier et al., *Somat. Cell Mol. Genet.,* 1992, 18, 233; Accession Number NM 006179), each of the references is incorporated herein by reference in its entirety. One skilled in the art can prepare antisense oligonucleotide molecules that will specifically bind a particular neurotrophin without cross-reacting with other polynucleotides. Preferred sites of targeting include, but are not limited to, the initiation codon, the 5' regulatory regions, the coding sequence and the 3' untranslated region. The oligonucleotides are preferably 10 to 100 nucleotides in length, more preferably 15 to 50 nucleotides in length, and more preferably 18 to 25 nucleotides in length. The oligonucleotides may comprise backbone modifications such as, for example, phosphorothioate linkages, and 2'-O sugar modifications well know to the skilled artisan. The oligonucleotides a can be administered intraperitoneally, intravenously, intramuscularly, subcutaneously, intrathecally, intraventricularly, orally, enterally, parenterally, intranasally, or dermally.

In other embodiments of the invention, the anti-neurotrophin agent is a small organic molecule directed to a neurotrophin. One skilled in the art can prepare small organic molecules that will specifically bind a particular neurotrophin without binding other polypeptides. Preferred sites of targeting include, but are not limited to, the portion of the neurotrophin that binds to the neurotrophin receptor and those portions of the neurotrophin molecule that are adjacent to the receptor-binding region and which are responsible, in part, for the correct three-dimensional shape of the receptor-binding portion. The small organic molecules preferably have a molecular weight of 100 to 20,000 daltons, more preferably 500 to 15,000 daltons, and more preferably 1000 to 10,000 daltons. Libraries of small organic molecules are commercially available. The small organic molecules can be administered intraperitoneally, intravenously, intramuscularly, subcutaneously, intrathecally, intraventricularly, orally, enterally, parenterally, intranasally, or dermally.

In other embodiments of the invention, the anti-neurotrophin agent is a dominant-negative mutant of a trk receptor. One skilled in the art can prepare dominant-negative mutants of a particular trk receptor such that the receptor will bind the naturally occurring neurotrophin and, thus, act as a "sink" to capture neurotrophins. The dominant-negative mutants, however, will not have the normal bioactivity of the trk receptor upon binding to a neurotrophin. Preferred dominant-negative mutants include, but are not limited, to the mutants described in the following: Li et al., *Proc. Natl. Acad. Sci. USA,* 1998, 95, 10884; Eide et al., *J. Neurosci.,* 1996, 16, 3123; Liu et al., *J. Neurosci,* 1997, 17, 8749; Klein et al., *Cell,* 1990, 61, 647; Valenzuela et al., *Neuron,* 1993, 10, 963; Tsoulfas et al., *Neuron,* 1993, 10, 975; and Lamballe et al., *EMBO J.,* 1993, 12, 3083, each of which is incorporated herein by reference in its entirety. The dominant negative mutants can be administered in protein form or in the form of an expression vector such that the mutant trk receptor is expressed in vivo. The protein or expression vector can be administered intraperitoneally, intravenously, intramuscularly, subcutaneously, intrathecally, intraventricularly, orally, enterally, parenterally, intranasally, or dermally. One skilled in the art is familiar with administration of expression vectors to obtain expression of an exogenous protein in vivo.

In some embodiments of the invention, the anti-neurotrophin agent comprises at least one neutralizing neurotrophin antibody. Preferred antibodies include all currently known neurotrophin antibodies including, but not limited to, anti-NGF (Catalog No. 500-P85, Pepro Tech Inc.; Catalog No. AF-256-NA, R&D Systems, Inc.), anti-BDNF (Catalog No. 500-P84, Pepro Tech Inc.; Catalog No. MAB248, R&D Systems, Inc.), anti-NT-3 (Catalog No. 500-P82, Pepro Tech Inc.; Catalog No. AF-267-NA, R&D Systems, Inc.), anti-NT4 (Catalog No. 500-P83, Pepro Tech Inc.; Catalog No. AF-268-NA, R&D Systems, Inc.), anti-NT-4/5, anti-NT-6 and anti-NT-7 and their functional equivalents. Preferably, these antibodies are used in an affinity purified form. Mixtures of two or more different neutralizing antibodies are also within the scope of the present invention. For instance, cancers such as pancreatic ductal adenocarcinoma, which express more than one type of neurotrophin receptor, may be treated more effectively with a mixture of antibodies to more than one receptor.

Antibodies of the present invention may be obtained from a commercial supplier, such as Pepro Tech, Inc. (Rocky Hill, N.J.), R&D Systems, Inc. (Minneapolis, Minn.) or generated according to standard procedures. Commercially available neutralizing neurotrophin antibodies include anti-human b-NGF, anti-human BDNF, anti-human NT-4, and anti-human NT-3 from rabbit antiserum.

Generation and purification of antibodies may also be conducted in the laboratory according to the standard procedures described in Ausubel, et al., 1999, *Short Protocols in Molecular Biology*, 4th Edition, Greene and Wiley-Interscience, NY and *Current Protocols in Molecular Biology*, 1999, John Wiley & Sons, NY, each of which is incorporated herein by reference in its entirety.

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for a neurotrophin or fragments thereof. Antibody fragments, including Fab, Fab', F(ab')$_2$, and F$_v$, are also provided by the invention. Screening assays to determine binding specificity of an antibody of the invention are well known and routinely practiced in the art. For a comprehensive discussion of such assays, see Harlow et al. (Eds.), Antibodies A Laboratory Manual, Cold Spring Harbor Laboratory, Cold Spring Harbor, N.Y. (1988), Chapter 6, which is incorporated herein by reference in its entirety. Antibodies that recognize and bind fragments of a neurotrophin are also contemplated. Antibodies of the invention can be produced using any method well known and routinely practiced in the art.

For example, recombinant or naturally occurring neurotrophin, or a fragment thereof, can be used to immunize a mouse, or other suitable animal, for generation of monoclonal antibodies (or larger mammal, such as a rabbit, for polyclonal antibodies). To increase antigenicity, peptides can be conjugated to keyhole lympet hemocyanin (Pierce), according to the manufacturer's recommendations. For an initial injection, the antigen can be emulsified with Freund's Complete Adjuvant and injected subcutaneously. At intervals of two to three weeks, additional aliquots of neurotrophin antigen can be emulsified with Freund's Incomplete Adjuvant and injected subcutaneously. Prior to the final booster injection, a serum sample can be taken from the immunized mice and assayed by Western blot to confirm the presence of antibodies that immunoreact with the neurotrophin. Serum from the immunized animals can be used as a polyclonal antisera or used to isolate polyclonal antibodies that recognize neurotrophin. Alternatively, the mice can be sacrificed and their spleen removed for generation of monoclonal antibodies.

To generate monoclonal antibodies, the spleens can be placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspensions can be filtered and washed by centrifugation and resuspended in serum-free RPMI. Thymocytes taken from three naive Balb/c mice are prepared in a similar manner and used as a feeder layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged, resuspended in RPMI containing 15% FBS, 100 μM sodium hypoxanthine, 0.4 μM aminopterin, 16 μM thymidine (HAT) (Gibco), 25 units/ml IL-6 (Boehringer-Mannheim) and 1.5× 10$^6$ thymocytes/ml, and plated into 10 Corning flat-bottom 96-well tissue culture plates (Corning, Corning N.Y.).

On days 2, 4, and 6 after the fusion, 100 μl of medium is removed from the wells of the fusion plates and replaced with fresh medium. On day 8, the fusions are screened by ELISA, testing for the presence of mouse IgG that binds to neurotrophin. Selected fusion wells are further cloned by dilution until monoclonal cultures producing anti-neurotrophin antibodies are obtained.

Non-human antibodies may be humanized by any of the methods known in the art. In one method, the non-human CDRs are inserted into a human antibody or consensus antibody framework sequence. Further changes can then be introduced into the antibody framework to modulate affinity or immunogenicity. Following are protocols to improve the utility of anti-neurotrophin monoclonal antibodies as therapeutics in humans by "humanizing" the monoclonal antibodies to improve their serum half-life and render them less immunogenic in human hosts (i.e., to prevent human antibody response to non-human anti-neurotrophin antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison et al., Adv. Immunol., 1989, 44, 65–92, which is incorporated herein by reference in its entirety). The variable domains of neurotrophin-neutralizing anti-neurotrophin antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. (See, e.g., Jones et al., *Nature*, 1986, 321, 522–525, Riechmann et al., *Nature*, 1988, 332, 323–327, Verhoeyen et al, *Science*, 1988, 239, 1534–36, and Tempest et al., *Bio/Technology*, 1991, 9, 266–71, each of which is incorporated herein by reference in its entirety. If necessary, the β-sheet framework of the human antibody surrounding the CDR3 regions also is modified to more closely mirror the three dimensional structure of the antigen-binding domain of the original monoclonal antibody. (See Kettleborough et al., *Protein Engin.*, 1991, 4, 773–783, and Foote et al., *J. Mol. Biol.*, 1992, 224, 487–499, each of which is incorporated herein by reference in its entirety).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, *Molecular Immunol*, 1991, 28, 489–98, which is incorporated herein by reference in its entirety.

The antibodies of the present invention may be formulated for administration to a mammal in a variety of ways. In some embodiments, the antibodies are in sterile aqueous solution or in biological fluids such as serum. Aqueous solutions may be buffered or unbuffered and have additional active or inactive components. Additional components include salts for modulating ionic strength, preservatives including, but not limited to, antimicrobials, anti-oxidants, chelating agents, and the like, and nutrients including glucose, dextrose, vitamins, and minerals. Alternatively, antibodies may be prepared for administration in solid form. The antibodies may be combined with a number of inert carriers or excipients, including but not limited to; binders such as microcrystalline cellulose, gum tragacanth or gelatin; excipients such as starch or lactose; dispersing agents such as alginic acid, Primogel, or corn starch; lubricants such as magnesium stearate; glidants such as colloidal silicon dioxide; sweetening agents such as sucrose or saccharin; or flavoring agents such as peppermint or methyl salicylate.

Antibodies or their formulations may be administered to a mammal by any means effective for delivering the antibodies to the diseased tissue. Such means include, but are not limited to, intraperitoneal, intravenous, intramuscular, subcutaneous, intrathecal, intraventricular, oral, enteral, parenteral, intranasal, or dermal. In particular, antibodies or antibody formulations may be administered by parenteral injection of liquid formulations or by ingestion of solid formulations such as in pills, tablets, capsules, or liquid formulations such as emulsions and solutions. Other drug delivery systems include hydrogels, hydroxmethylcellulose, microcapsules, liposomes, microemulsions, microspheres, and the like. Localized injection of antibodies directly into diseased tissue such as a tumor is a preferred method for administering antibodies of the present invention. Phosphate buffered saline (PBS) is a preferred carrier for injectable formulations.

Dosing of antibodies to obtain a pharmaceutically effective amount of therapeutic agent depends on a variety of factors. For example, age, sensitivity, tolerance, and other characteristics of the patient will affect dosing amounts. The type of neoplasia or tumor, the stage of the disease, and tumor volume will also affect dosages. Furthermore, plasma level and half-life of the antibodies employed and affinity for their recognition sites, and other similar factors routinely considered by an attending physician need to be considered for effective dosing. For systemic administration of the neurotrophin antibodies, doses ranging from about 0.05 mg/kg-patient/day to about 500 mg/kg-patient/day can be used, although dosages in the lower end of the range are preferred simply for ease of administration and cost effectiveness. Dosages may be adjusted, for example, to provide a particular plasma level of an antibody, e.g., in the range of about 5–30 mg/ml, more preferably about 10–15 mg/ml, and to maintain that level, e.g., for a period of time or until clinical results are achieved. Chimeric and humanized antibodies, which would be expected to be cleared more slowly, would require lower dosages to maintain an effective plasma level. Also, antibodies having high affinity for neurotrophins preferably are administered less frequently or in lower doses than antibodies with less affinity. A therapeutically effective dosage of antibody can be determined by showing, during the course of treatment, reduction in tumor volume, reduction in growth rate of the tumor, or, ideally, complete disappearance of the cancerous disease state. Effective means for measuring or evaluating the stage of prostate or pancreatic cancer is by measuring the prostate specific antigen (PSA) in the blood, measuring survival time for pancreatic cancer, measuring the delay or inhibition of metastatic spread for both prostate and pancreatic cancer, measuring the histological grading of pancreatic cancer, and CT for pancreatic cancer. Such procedures are known to the skilled artisan.

The present invention also contemplates a method for reducing prostatic or pancreatic tumor volume by contacting the tumor with at least one anti-neurotrophin agent. The present invention also encompasses a method for preventing further tumor growth or reducing tumor growth rate by contacting the tumor with at least one anti-neurotrophin agent. Delivery of the agent to the tumor site is preferably accomplished through direct, localized injection into the tissue at or near the tumor site. Systemic administration of agents by means discussed above, however, is also within the scope of the present invention. Local injection at the site of the tumor may occur intratumorally or peritumorally or a combination of both.

For direct injection at the tumor site, dosage of agent depends on several factors including type of tumor, stage of tumor, and tumor volume among other variables. Typical therapeutic doses of agents according to tumor volume may range from about 0.01 mg/mm$^3$ to about 10 mg/mm$^3$ per injection, and injections may be administered as frequently as needed. For example, injections once a day for the time a tumor or disease state is present may be appropriate but will vary according to the type of cancer, course of the disease, and patient. Therapeutic effectiveness of the treatment is indicated by either a reduction in tumor volume during the course of treatment or an inhibition in tumor growth rate. Measurement of tumor volume from tumor dimensions is well known to those skilled in the art. Tumor volume calculations can be made with the following formula: $V(mm^3)=0.5236 \times length(mm) \times width(mm)$ [length (mm)+width(mm)/2].

Another method of evaluating the effectiveness of a particular treatment is to evaluate inhibition of neurotrophin receptors by means well known in the art. For instance, trkA can be tested for activity using an ELISA-based enzyme assay as set forth in Angeles, et al., *Anal Biochem.*, 1996, 236, 49, incorporated herein by reference in its entirety. Another method of evaluation is to measure ChAT activity in the rat basal forebrain.

In other embodiments of the invention, anti-neurotrophin agents are administered to a mammal to prevent or reduce pain. The agents, amounts, and administration thereof are described above.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The following examples are all actual and are not intended to limit the scope of the invention.

EXAMPLES

Example 1

Neutralization of trk Receptors by Anti-NGF

Antibodies were injected into PC-3 and/or TSU-pr1 xenografts which have been shown previously to respond to CEP-751 (Dionne et al., *Clin. Canc. Res.*, 1998, 4, 187–1898). The following experiments were carried out to confirm the neutralizing capability of the anti-neurotrophin antibodies.

Anti-NGF antibody reduces ligand-stimulated autophosphorylation of trk in NIH3T3-trkA cells. NGF (10 ng/ml) was preincubated with varying concentrations of antibody in 6 ml of tissue culture media. The NGF/antibody mix was added to NIH3T3-trkA cells. Trk proteins were immunoprecipitated from the lysates with pan-Trk antibody CEP-21, and the samples were probed on an immunoblot with the anti-phosphotyrosine antibody 4G10. Densitometric scanning values (integrated OD units) were as follows (shown as NGF (10 ng/ml)/Anti-NGF ($\mu$g/ml): –/–lane, 0.3; +/–lane, 6.5; 0.001 mg/ml, 5.0; 0.01 mg/ml, 4.5; 0.1 mg/ml, 2.5; 1.0 mg/ml, 3.1; 10.0 mg/ml, 2.1; 100 mg/ml, 1.1. Thus, anti-NGF (PeproTech, Inc., 500-P85) at 100 $\mu$g/ml reduces trk phosphorylation approximately 80% relative to no anti-NGF treatment in cells treated for five minutes with 10 ng/ml NGF.

Example 2

Neutralization of trk Receptors by Anti-NT-3

Anti-NT-3 antibody reduces ligand-stimulated autophosphorylation of trk in NIH3T3-trkC cells. NT-3 (10 ng/ml) was preincubated with varying concentrations of antibody in 6 ml of tissue culture media. The NT-3/antibody mix was added to NIH3T3-trkC cells. Trk proteins were immunoprecipitated from the lysates with pan-Trk antibody CEP-21, and the samples were probed on an immunoblot with the anti-phosphotyrosine antibody 4G10. Densitometric scanning values (integrated OD units) were as follows (shown as NT-3 (10 ng/ml)/Anti-NT-3 ($\mu$g/ml): –/–lane, 0.1; +/–lane, 4.0; IgG, 7.5; 0.001 mg/ml, 6.2; 0.01 mg/ml, 4.0; 0.1 mg/ml, 3.6; 1.0 mg/ml, 7.8; 10.0 mg/ml, 1.2. Thus, anti-NT-3 (PeproTech 500-P82) at 10 $\mu$g/ml reduces trk phosphorylation approximately 70% relative to no anti-NGF treatment in cells treated for five minutes with 10 ng/ml NT-3.

The following examples show experimental results for anti-tumor activity of the antibodies of the present invention. Tumor models used in these experiments are prostate cancer and pancreatic cancer xenografts in nude mice that are well known to those skilled in the art as preferred pre-clinical animal models, which are correlative to in vivo clinical results. Current references indicating the particular relevance of these xenograft models to the corresponding human diseases include Plonowski, et al., *Cancer Res.*, 1999, 59, 1947, Joseph, et al., *Cancer Res.*, 1997, 57, 1054, Pinski, et al., *Int. J. Cancer,* 1993, 55, 963, Gao et al., *Cancer Res.*, 1998, 58, 1391, and Tan, et al., *Tumour Biology,* 1985, 6, 89.

Example 3

Inhibition of PC-3 Prostate Cancer Xenograft Growth by Neurotrophin Antibodies

The following neurotrophin antibodies were used: anti-NGF (PeproTech 500-P85), anti-BDNF (PeproTech 500-P84), anti-NT-3 (PeproTech 500-P82), and anti-NT4/5 (PeproTech 500-P83). The anti-NGF and anti-NT3 antibodies block trkA and trkC autophosphorylation following neurotrophin treatment of cultured cells. Each of the antibodies has been shown to block the activity of its cognate neurotrophin in a bioassay in which ChAT activity is measured in rat basal forebrain cell cultures.

PC-3 human prostate tumor cells (5×10$^6$ cells/mice) were injected subcutaneously into the flank of eight to ten week old, female athymic nude mice (nu/nu; Charles River, Raleigh, N.C.). Mice weighed between 22–25 grams on the day of tumor implantation. Upon xenografts reaching 100–500 mm$^3$, the mice were randomized and divided into experimental groups. Some experimental groups were administered a cocktail of neurotrophin antibodies (4×25 $\mu$g each, or 4×100 $\mu$g each of anti-NGF, BDNF, NT-3, and NT4/5) or normal rabbit IgG (100 $\mu$g or 400 $\mu$g; PeproTech 500-P00) in sterile 1×PBS (total volume of 100 $\mu$l). All antibodies were administered intratumorally (50 $\mu$l) at five injection sites and peritumorally, subcutaneously (50 $\mu$l) at five injection sites. In experiment #1, the mice received injections of antibody once a day on days 1, 3, 5, 8, 10, 12, and 15. No antibody was administered after day 15. In experiment #2, the mice received injection of antibody once a day on days 1, 3, 6, 8, 10, 13. One mouse receiving 4×100 $\mu$g of neurotrophin antibodies died of unexplained causes on day 13. Tumor length and width were measured every two to three days. CEP-751 was administered to a separate experimental group as a control to verify that the tumors were responsive to CEP-751, as has been shown previously for PC-3 xenografts grown at a different institution. The mice received vehicle (40% polyethylene glycol, 10% povidone C30, and 2% benzyl alcohol; 100 $\mu$l) or CEP-751 (10 mg/kg s.c. BID) in vehicle (100 $\mu$l) seven days per week for 22 days. Tumor length and width were measured every two to three days (days 1, 3, 5, 8, 10, 12, 15, 17, 19 and 22).

Tumor volumes were calculated as (length×width (length+width)/2))×0.526 (Isaacs, *Canc. Res.,* 1989, 49, 6290–6294, which is incorporated herein by reference in its entirety). The mean tumor volumes and standard errors were calculated (SigmaStat, Jandel Scientific, San Rafel, Calif.). Any mouse with a tumor volume on the final day of analysis that deviated from the mean tumor volume on the final day of analysis by more than two standard deviations was removed from the analysis at every data point. Relative tumor volumes were calculated as (mean v$_t$ mean v$_o$), where v$_t$ refers to tumor volume on a given day and v$_o$ is the volume of the same tumor at initiation of dosing (day 1). Any mouse with a relative tumor volume on the final day of analysis that deviated from the mean relative tumor volume on the final day of analysis by more than two standard deviations was removed from the analysis at every data point. Probability values were calculated by the Mann-Whitney Rank Sum Test (SigmaStat).

Experiment #1 Administration of the neurotrophin antibodies inhibited the growth of PC-3 tumors relative to tumors treated with the IgG control. The relative volumes of the tumors treated with neurotrophin antibody were significantly smaller (p$\leq$0.05) than the IgG control group by day 3 and remained smaller until the termination of the experiment on day 22 (p$\leq$0.05, day 5, p$\leq$0.01, day 8; p$\leq$0.001, days 10–22). Significant regression of tumors was observed on days 10 (35%; p$\leq$0.001) and 12 (25%; p$\leq$0.05). After neutralizing antibody treatment was withdrawn (day 15), tumor re-growth was observed by day 22, (0.95 relative tumor volume, day 22, vs. 0.77 relative tumor volume, day 15). The absolute volumes of the tumors treated with neurotrophin antibody compared with the IgG control group were significantly smaller (p$\leq$0.05) by day 15, remained smaller until the termination of the experiment (p$\leq$0.05, day 17; p$\leq$0.01, days 19 and 22), and reached a minimum T/C of 0.33 on day 17.

Administration of CEP-751 inhibited the growth of PC-3 tumors relative to vehicle control. The relative volumes of the tumors treated with CEP-751 were significantly smaller than the vehicle control group on days 12 (p$\leq$0.05), 17 (p$\leq$0.01), 19 (p$\leq$0.05) and 22 (p$\leq$0.01). The absolute volumes of tumors treated with CEP-751 were significantly smaller compared with the vehicle control group on day 17 (p≦0.01) and day 22 (p≦0.05) and reached a minimum T/C of 0.44 by day 19.

Experiment #2 Administration of the antibodies (4×25 μg each, or 4×100 μg each of anti-NGF, BDNF, NT-3, and NT4/5) inhibited the growth of PC-3 tumors relative to tumors treated with the IgG control. The relative volumes of the tumors treated with neurotrophin antibody were significantly smaller (p≦0.05; 100 mg neurotrophin cocktail vs. 100 μg normal IgG; 400 μg neurotrophin cocktail vs. 400 μg normal IgG) than the IgG control groups by day 3 and remained smaller until the termination of the experiment. Significant regression of tumors (400 μg neurotrophin cocktail vs. 400 μg normal IgG) was observed on day 10 (31%; p≦0.05) and day 13 (19%; p≦0.05). The absolute volumes of the tumors treated with neurotrophin antibody compared with the IgG control group were significantly smaller (p≦0.05) by day 8 (100 μg neurotrophin cocktail vs. 100 μg normal IgG) and day 6 (400 μg neurotrophin cocktail vs. 400 μg normal IgG), remained smaller until the termination of the experiment (p≦0.005, days 10, 13, 15 for both 100 μg neurotrophin cocktail vs. 100 μg normal IgG and 400 μg neurotrophin cocktail vs. 400 μg normal IgG), and reached a minimum T/C of 0.26 on day 15 (100 μg neurotrophin cocktail vs. 100 μg normal IgG) or a minimum T/C of 0.17 on day 13 (400 μg neurotrophin cocktail vs. 400 μg normal IgG).

Example 4

Inhibition of TSU-Pr1 Prostate Cancer Xenograft Growth by Neurotrophin Antibodies Experiment #1 The following neurotrophin antibodies were used: anti-NGF (PeproTech 500-P85), anti-BDNF (PeproTech 500-P84), anti-NT-3 (PeproTech 500-P82), and anti-NT4/5 (PeproTech 500-P83).

TSU-Pr1 human prostate tumor cells were injected subcutaneously into the flank of female athymic nude mice (nu/nu; 5×10$^6$ cells/mice). Upon xenografts reaching 100–500 mm$^3$, the mice were randomized and divided into four experimental groups. One group was administered a cocktail of neurotrophin antibodies (anti-NGF, BDNF, NT-3, and NT4/5). Each dose of antibody cocktail (100 μl) contained 100 μg of each neurotrophin antibody. The second experimental group was administered normal rabbit IgG (400 μg/100 μl; PeproTech 500-P00) as a control. All antibodies were administered intratumorally (50 μl) at five injection sites and peritumorally (50 μl) at five injection sites. The mice received injections of antibody once a day, three days per week on Days 1, 3, 5, 8, 10, and 12. Tumor length and width were measured every two to three days (Days 1, 3, 5, 8, 10, 12, and 15).

The third experimental group received CEP-701 in vehicle (40% polyethylene glycol, 10% povidone C30, and 2% benzyl alcohol), 10 mg/kg sc BID, five days per week for 14 days. The fourth experimental group received vehicle only (100 μl) according to the dosing schedule of the third experimental group. Tumor length and width were measured every two to three days (Days 1, 3, 5, 8, 10, 12, and 15).

Tumor volumes were calculated as described above. The mean tumor volumes and standard errors were calculated as described above. Any mice with tumor volumes that deviated from the mean tumor volumes by more than two standard deviations were removed from the analysis at every data point. For relative tumor volumes, each data point for a given mouse was normalized to the tumor volume of that mouse at the initiation of dosing (Day 1). Probability values were calculated as described above. No deaths or morbidity were observed in any of the experimental groups, indicating that CEP-701 and the neutralizing antibodies are well tolerated in these animals.

Administration of the neurotrophin antibodies resulted in lower relative tumor volumes relative to tumor volumes in the IgG control group. The relative tumor volumes of the tumors treated with neurotrophin antibody were significantly smaller (p≦0.0001) than the relative tumor volumes in the IgG treated control group by Day 5 and remained smaller throughout the remainder of the experiment (p≦0.01 Days 8 and 10; p≦0.0001 Days 12 and 15). The absolute volumes of tumors treated with neurotrophin antibody compared with the IgG control group were significantly smaller (p≦0.05) by Day 10, remained smaller until the termination of the experiment (p≦0.001, Day 12; p≦0.01, Day 15) and reached a minimum T/C of 0.41 on Day 15.

Administration of CEP-701 resulted in lower relative tumor volumes relative to tumor volumes in the vehicle control group. The relative tumor volumes of the tumors treated with CEP-701 were significantly smaller (p≦0.05) by Day 3 than the vehicle treated control group and remained smaller until the termination of the experiment (p≦0.01, Day 5; p≦0.05, Day 8; p≦0.01 Day 10 and 12; p≦0.001 Day 15). The absolute volumes of tumors treated with CEP-701 were significantly smaller compared with the vehicle control group on Day 8 (p≦0.05), remained smaller until the termination of the experiment (p≦0.05, Day 10; p≦0.001 Days 12 and 15), and reached a minimum T/C of 0.29 on Days 12 and 15.

The tumors treated with the normal IgG appear to have grown more slowly than those treated with the vehicle for CEP-701; however, there was not a significant (p≦0.05) difference in tumor volumes or relative tumor volumes between these two groups at any time during the experiment.

This experiment demonstrates that neurotrophin antibodies inhibit TSU-Pr1 xenograft growth. The relative tumor volumes of the tumors treated with neutralizing antibodies were significantly smaller than the normal IgG treated control group on Day 5 (p≦0.0001), Days 8 and 10 (p≦0.01), and Days 12 and 15 (p≦0.0001). Since the neurotrophin antibodies inhibited tumor growth relative to normal IgG, it is likely that the effect of the neurotrophin antibodies is due to blocking neurotrophin signaling through the trk neurotrophin receptors, as opposed to a general effect from the injection of IgG into tumors.

Experiment #2 The following neurotrophin antibodies were used: anti-NGF (PeproTech 500-P85), anti-BDNF (PeproTech 500-P84), anti-NT-3 (PeproTech 500-P82), and anti-NT4/5 (PeproTech 500-P83).

TSU-Pr1 human prostate tumor cells were injected subcutaneously into the flank of female athymic nude mice (nu/nu; 5×10$^6$ cells/mice). Upon xenografts reaching 100–500 mm$^3$, the mice were randomized and divided into six experimental groups. The first group was administered anti-NGF (100 μg)+normal rabbit IgG (300 μg) per dose. The second group was administered anti-NT-3 (100 μg)+normal rabbit IgG (300 μg) per dose. The third group was administered anti-NT4/5 (100 μg)+normal rabbit IgG (300 μg) per dose. The fourth group was administered anti-BDNF (100 μg)+normal rabbit IgG (300 μg) per dose. The fifth group was administered a cocktail of neurotrophin antibodies ((anti-NGF, BDNF, NT-3, and NT4/5 (100 μg each antibody per dose)). The sixth experimental group was administered normal rabbit IgG (400 μg per dose; PeproTech 500-P00) as a control. Each dose (400 μg total protein per 100 μl PBS) was injected intratumorally (50 μl) at five injection sites and peritumorally (50 μl) at five injection sites, once a day, three days per week on Days 1, 3, 6, 8, 10, and 13. Tumor length and width were measured every two to three days (Days 1, 3, 6, 8, 10, 13, and 15).

Tumor volumes were calculated as described above. The mean tumor volumes and standard errors were also calculated as described above. Any mice with tumor volumes that deviated from the mean tumor volumes by more than two standard deviations were removed from the analysis at every data point. For relative tumor volumes, each data point for a given mouse was normalized to the tumor volume of that mouse at the initiation of dosing (Day 1). Probability values were calculated as described above. No deaths or morbidity were observed in any of the experimental groups, indicating that the neutralizing antibodies are well tolerated in these animals.

The cocktail of neurotrophin antibodies (anti-NGF, anti-NT-3, anti-BDNF, and anti-NT-4/5), anti-NGF, or anti-NT-3 inhibited tumor growth relative to normal rabbit IgG. Neither anti-NT-4/5 nor anti-BDNF had a significant effect on tumor growth relative to normal rabbit IgG. The relative tumor volumes for the group that received the neurotrophin antibody cocktail were significantly smaller than the relative tumor volumes for the IgG control group by Day 3 ($p \leq 0.01$) and Day 8 ($p \leq 0.05$), then remained smaller throughout the remainder of the experiment ($p \leq 0.01$ Days 10, 13, and 15). The relative tumor volumes of the tumors treated with anti-NGF were significantly smaller ($p \leq 0.001$) than the relative tumor volume in the IgG treated control group by Day 3 and remained smaller throughout the remainder of the experiment ($p \leq 0.001$ Day 6; $p \leq 0.01$ Day 8; $p \leq 0.001$ Day 10; $p \leq 0.01$ Day 13; $p \leq 0.001$ Day 15). The relative tumor volume of the tumors treated with anti-NT-3 were significantly smaller ($p \leq 0.05$) than the tumors in the IgG control group by Day 6 and remained smaller throughout the remainder of the experiment ($p \leq 0.01$ Day 8; $p \leq 0.001$ Day 10; $p \leq 0.01$ Day 13; $p \leq 0.001$ Day 15).

The absolute tumor volumes of the neurotrophin antibody cocktail group were significantly smaller ($p \leq 0.05$, Day 8; $p \leq 0.01$, Days 10, 13, and 15) as compared to the IgG treated control group and reached a minimum T/C of 0.52 on Day 13. The absolute tumor volumes of the group which received anti-NGF were significantly smaller ($p \leq 0.05$, Day 3; $p \leq 0.001$, Days 6, 8, 10, 13; and $p \leq 0.01$ Day 15) as compared to the IgG treated control group and reached a minimum T/C of 0.34 by Day 13. Regression was observed in the anti-NGF group on Day 3 (20%, $p \leq 0.001$), Day 6 (31%, $p \leq 0.01$), Day 8 (35%, $p \leq 0.001$), Day 10 (35%, $p \leq 0.01$), and Day 13 (37%, $p \leq 0.01$). The absolute tumor volumes of the group which received anti-NT-3 were significantly smaller ($p \leq 0.05$, Day 6; $p \leq 0.0.1$ Days 8, 10, 13, and 15) as compared to the IgG treated controls and reached a minimum T/C of 0.38 by Day 13. Regression was observed in the anti-NT-3 group on Day 8 (16%, $p \leq 0.001$), Day 10 (33%, $p \leq 0.001$), and Day 13 (29%, $p \leq 0.01$).

A comparison of the effects of anti-NGF or anti-NT-3 relative to the neurotrophin antibody cocktail demonstrated that each of these individual neurotrophin antibodies transiently inhibited tumor growth more effectively than the neurotrophin antibody cocktail. The relative and absolute tumor volumes of the anti-NGF group were significantly smaller than the neurotrophin antibody cocktail group on Day 8 ($p \leq 0.01$) and Day 10 ($p \leq 0.05$). The anti-NGF inhibited tumor growth by 57 and 64 percent relative to normal rabbit IgG on Days 8 and 10, respectively, while the neurotrophin antibody cocktail inhibited growth by 32 and 43 percent relative to normal rabbit IgG on Days 8 and 10, respectively. The relative tumor volume of the anti-NT-3 group was significantly smaller than the neurotrophin antibody cocktail group on Day 10 ($p \leq 0.05$). The anti-NT-3 inhibited tumor growth by 60 percent relative to normal rabbit IgG on Day 10, while the neruotrophin antibody cocktail inhibited growth by 43 percent relative to normal rabbit IgG on Day 10. The results from this experiment demonstrate that anti-NGF or anti-NT-3 inhibits the growth of TSU-Pr1 xenografts as well as, and transiently better than, the neurotrophin antibody cocktail (anti-NGF, anti-NT-3, anti-BDNF, and anti-NT-4/5).

At a dose of 100 μg, neither anti-NT-4/5 nor anti-BDNF had a significant effect on the growth of TSU-Pr1 tumors in nude mice, although it is possible that different NT-4/5 or BDNF neutralizing antibodies or a different concentration of these antibodies could result in a significant effect on tumor growth. Previous data analyzing trkB expression in TSU-Pr1 cells showed that trkB is not expressed in this cell line (Dionne, et al., 1998). Since BDNF and NT-4/5 mainly signal through trkB (Barbacid, 1995; Ibanez, 1995), the lack of effect observed in our experiment is consistent with the absence of the receptor.

Example 5

Inhibition of AsPC-1 Pancreatic Cancer Xenograft Growth by Neurotrophin Antibodies The following neurotrophin antibodies were used: anti-NGF (PeproTech 500-P85), anti-BDNF (PeproTech 500-P84), anti-NT-3 (PeproTech 500-P82), and anti-NT4/5 (PeproTech 500-P83).

AsPC-1 human pancreatic tumor cells were injected subcutaneously into the flank of female athymic nude mice (nu/nu; $5 \times 10^6$ cells/mice). Upon xenografts reaching 100–500 mm$^3$, the mice were randomized and divided into four experimental groups. One group was administered a cocktail of neurotrophin antibodies (anti-NGF, BDNF, NT-3, and NT4/5). Each dose of antibody cocktail (100 μl) contained 100 μg of each neurotrophin antibody. The second experimental group was administered normal rabbit IgG (400 μg/100 μl; PeproTech 500-P00) as a control. All antibodies were administered intratumorally (50 μl) at five injection sites and peritumorally (50 μl) at five injection sites. The mice received injections of antibody once a day, three days per week on Days 1, 3, 5, 8, 10, and 12. Tumor length and width were measured every two to three days (Days 1, 3, 5, 8, 10, 12, and 15). The third experimental group received CEP-701 in vehicle (40% polyethylene glycol, 10% povidone C30, and 2% benzyl alcohol), 10 mg/kg sc BID, five days per week for 14 days. The fourth experimental group received vehicle only (100 μl) according to the dosing schedule of the third experimental group. Tumor length and width were measured every two to three days (Days 1, 3, 5, 8, 10, 12, and 15).

Tumor volumes were calculated as described above. The mean tumor volumes and standard errors were also calculated as described above. Any mice with tumor volumes that deviated from the mean tumor volumes by more than two standard deviations were removed from the analysis at every data point. For relative tumor volumes, each data point for a given mouse was normalized to the tumor volume of that mouse at the initiation of dosing (Day 1). Probability values were calculated as described above. No deaths or morbidity were observed in any of the experimental groups, indicating that CEP-701 and the neutralizing antibodies are well tolerated in these animals.

Administration of the neurotrophin antibodies resulted in lower relative tumor volumes compared with tumor volumes in the IgG control group. The relative tumor volumes of the tumors treated with neurotrophin antibody were significantly smaller ($p \leq 0.05$) than the IgG treated control group on Days 5, 10, 12 and 15. The absolute volumes of tumors treated with neurotrophin antibody compared with the IgG control group were significantly smaller ($p \leq 0.01$) by Day 5, remained smaller until the termination of the experiment ($p \leq 0.01$, Days 8, 10, 12, and 15), and reached a minimum T/C of 0.43 on Day 15.

Administration of CEP-701 resulted in lower relative tumor volumes compared with tumor volumes in the vehicle control group. The relative tumor volumes of the tumors treated with CEP-701 were significantly smaller ($p \leq 0.01$) than the vehicle treated control group by Day 3 and remained smaller until the termination of the experiment ($p \leq 0.001$, Day 5; $p \leq 0.01$, Day 8; $p \leq 0.001$ Day 10, $p \leq 0.01$ Day 12; and $p \leq 0.001$ Day 15) The absolute volumes of tumors treated with CEP-701 were significantly smaller compared with the vehicle control group on Day 5 ($p \leq 0.05$), remained smaller until the termination of the experiment ($p \leq 0.05$, Days 8, 10, 12, and 15), and reached a minimum T/C of 0.27 on Day 15.

This experiment demonstrates that neurotrophin antibodies inhibit AsPC-1 xenograft growth. Since the neurotrophin antibodies inhibited tumor growth relative to normal IgG, it is likely that the effect of the neurotrophin antibodies is due to blocking neurotrophin signaling through the trk neurotrophin receptors, as opposed to a general effect from the injection of IgG into tumors. The tumors treated with the normal IgG appear to have grown more slowly than those treated with the vehicle for CEP-701; however, there was not a significant ($p \leq 0.05$) difference in tumor volumes or relative tumor volumes between these two groups at any time during the experiment.

Example 6

Comparative Results for CFPAC Pancreatic Tumor Xenografts Treated with Neurotrophin Antibodies The following neurotrophin antibodies were used: anti-NGF (PeproTech 500-P85), anti-BDNF (PeproTech 500-P84), anti-NT-3 (PeproTech 500-P82), and anti-NT4/5 (PeproTech 500-P83).

The human pancreatic carcinoma cell lines AsPC-1 and CFPAC were grown in RPMI, or DMEM media respectively, (Cellgro/Mediatech, Washington, D.C.) containing 10% fetal bovine serum (Atlanta Biologicals, Norcoss, Ga.) at 37° C. in a humidified incubator, with 95% air/5% $CO_2$ atmosphere. The cells were determined to be free of mycoplasma and rodent viruses (MAP testing). Exponentially growing cells were harvested using trypsin/EDTA (GibcoBRL, Rockville, Md.), and counted using trypan blue (Fisher Scientific, Malvern, Pa.). The cells were resuspended in the appropriate growth media 1:1 with Matrigel (Fisher Scientific).

Female athymic nu/nu mice (8–10 weeks old; Charles River, Raleigh, N.C.) were maintained at five per cage in microisolator units. Animals were given a commercial diet and water ad libitum, housed at 48±2% humidity and 22±2° C., and light-dark cycle was set at 12 hour intervals. Mice were quarantined for at least 1 week before experimental manipulation. Mice weighed between 22 and 25 g on the day of inoculation of tumor cells. Exponentially growing cells, which were cultured as described above, were harvested and injected ($5 \times 10^6$ cells/mouse) into the right flank of nude mice. Animals bearing tumors of 100–400 mm³ (AsPC-1) or 100–900 mm³ (CFPAC) ten days postinoculation were randomized into the appropriate groups. Treatment was initiated with a cocktail of neurotrophin neutralizing antibodies (anti-NGF, anti-BDNF, anti-NT-3, and anti-NT4/5; 100 µg of each antibody in a total volume of 100 µl, 50 µl intratumorally and 50 µl peritumorally) or normal rabbit IgG (400 µg/100 µl, 50 µl intratumorally and 50 µl peritumorally). The mice received injections of antibodies or normal rabbit IgG once a day, three days per week on Days 1, 3, 5, 8, 10, and 12.

Tumors were measured every 2–4 days using a vernier caliper. Tumor volumes were calculated as described above. The mean tumor volumes and standard errors were also calculated as described above. Any mouse with a tumor volume on the final day of analysis that deviated from the mean tumor volume on the final day of analysis by more than two standard deviations was removed form the analysis at every data point. Statistical analyses were calculated as described above with $p \leq 0.05$ deemed significant.

Administration of the neurotrophin antibodies (anti-NGF, anti-BDNF, anti-NT-3, and anti-NT4/5) to AsPC-1 xenografts resulted in lower relative tumor volumes compared with tumor volumes in the IgG control group. The relative tumor volumes of the tumors treated with neurotrophin antibody were significantly smaller ($p \leq 0.05$) than the IgG treated control group starting on Day 5 and remained smaller from Day 10 until the termination of the experiment. The absolute volumes of tumors treated with neurotrophin antibody compared with IgG treated control animals were significantly smaller ($p \leq 0.01$) by Day 5, remained smaller until the termination of the experiment, and reached a maximum 55 percent inhibition of tumor growth on Day 15.

Administration of the neurotrophin neutralizing antibodies did not inhibit the growth of CFPAC tumors relative to tumors treated with the IgG control. The lack of inhibition by the neurotrophin neutralizing antibodies suggests that these xenografts are not dependent on neurotrophins for growth. The CFPAC unresponsiveness is consistent with previously published data that CFPAC tumor growth was insensitive to treatment with the pan-trk inhibitor CEP-701, whereas the growth of AsPC-1 tumors was inhibited by CEP-701.

There were no apparent signs of neutralizing antibody related morbidity or deaths in the experimental group, and body weights were comparable between animals treated with neutralizing antibody and animals treated with normal rabbit IgG (Tables 2 & 4). These data indicate that neutralizing antibodies were well tolerated by the animals at doses in which significant anti-tumor efficacy was observed.

TABLE 1

Anti-tumor Effect of Neutrophin Neutralizing Antibodies on ASPC1 Pancreatic Xenografts in Nude Mice: Relative Tumor Volume (Absolute Tumor Volume)

| Group | Neutralizing Antibody (100 µg each Ab/100 µl) | Normal Rabbit IgG (400 µg/100 µl) |
|---|---|---|
| Day 1 | 1.0 ± 0.0 (212.60 ± 21.30) n = 10 | 1.0 ± 0.0 (203.90 ± 19.30) n = 9 (n = 10) |

TABLE 1-continued

Anti-tumor Effect of Neurotrophin Neutralizing Antibodies on ASPC1 Pancreatic Xenografts in Nude Mice: Relative Tumor Volume (Absolute Tumor Volume)

| Group | Neutralizing Antibody (100 μg each Ab/100 μl) | Normal Rabbit IgG (400 μg/100 μl) |
| --- | --- | --- |
| Day 3 | 1.14 ± 0.17 (225.57 ± 25.53) n = 10 | 1.39 ± 0.16 (276.13 ± 41.25) n = 9 (n = 10) |
| Day 5 | 1.12 ± 0.24* (208.66 ± 28.45**) n = 10 | 1.70 ± 0.18 (340.29 ± 45.54) n = 9 (n = 10) |
| 0.0.1 Day 8 | 1.23 ± 0.22 (228.87 ± 24.72**) n = 10 | 1.87 ± 0.20 (381.04 ± 50.90) n = 9 (n = 10) |
| Day 10 | 1.123 ± 0.31* (199.98 ± 41.90**) n = 10 | 2.12 ± 0.25 (432.43 ± 51.02) n = 9 (n = 10) |
| Day 12 | 1.341 ± 0.41* (238.87 ± 58.90**) n = 10 | 2.64 ± 0.35 (520.87 ± 63.49) n = 9 (n = 10) |
| Day 15 | 1.66 ± 0.47* (296.31 ± 64.43**) n = 10 | 3.06 ± 0.42 (659.38 ± 89.35) n = 9 (n = 10) |

Nude mice bearing ASPC1 tumors were treated with neutralizing antibody (100 μg each Ab/100 μl, intratumorally and peritumorally qd on Days 1, 3, 5, 8, 10, and 12) or normal rabbit IgG in sterile PBS (100 μg/100 μl intratumorally and peritumorally qd on Days 1, 3, 5, 8, 10, and 12). Tumor volumes were determined every 2–3 days. Values are Mean±SE of relative tumor volume. Values in parentheses are Mean±SE actual tumor volume ($mm^3$). *$p \leq 0.05$, **$p \leq 0.01$ by Mann-Whitney Rank Sum Test.

TABLE 2

The Effects of Neurotrophin Neutralizing Antibodies on the Body Weights of Nude Mice Bearing AsPC-1 Xenografts

| Group | Neutralizing Antibody (100 μg each Ab/100 μl) | Normal Rabbit IgG (400 μg/100 μl) |
| --- | --- | --- |
| Day 1 | 23.1 ± 0.3 n = 10 | 23.3 ± 0.3 n = 10 |
| Day 3 | 22.9 ± 0.3 n = 10 | 22.1 ± 0.3 n = 10 |
| Day 5 | 22.9 ± 0.4 n = 10 | 23.5 ± 0.3 n = 10 |
| Day 8 | 22.9 ± 0.3 n = 10 | 23.4 ± 0.5 n = 10 |
| Day 10 | 23.0 ± 0.2 n = 10 | 22.9 ± 0.2 n = 10 |
| Day 12 | 22.8 ± 0.3 n = 10 | 23.3 ± 0.4 n = 10 |
| Day 15 | 24.4 ± 0.4 n = 10 | 24.3 ± 0.4 n = 10 |

Nude mice bearing ASPC1 tumors were treated with neutralizing antibody (100 μg each Ab/100 μl, intratumorally and peritumorally qd on Days 1, 3, 5, 8, 10, and 12), or normal rabbit IgG in sterile PBS (100 μg/100 μl intratumorally and peritumorally qd on days 1, 3, 5, 8, 10, and 12). Values are Mean±SE of body weight.

TABLE 3

Effect of Neurotrophin Neutralizing Antibodies on CFPAC Pancreatic Xenografts in Nude Mice: Relative Tumor Volume (Absolute Tumor Volume)

| Group | Neutralizing Antibody (100 μg each Ab/100 μl) | Normal Rabbit IgG (400 μg/100 μl) |
| --- | --- | --- |
| Day 1 | 1.0 ± 0.0 (430.9 ± 88.3) n = 8 (n = 9) | 1.0 ± 0.0 (430.6 ± 81.4) n = 8 (n = 9) |
| Day 4 | 1.34 ± 0.10 (587.68 ± 136.78) n = 8 (n = 9) | 1.24 ± 0.07 (530.76 ± 91.3) n = 8 (n = 9) |
| Day 8 | 2.07 ± 0.24 (899.45 ± 243.6) n = 8 (n = 9) | 2.12 ± 0.18 (850.7 ± 157.1) n = 8 (n = 9) |
| Day 10 | 2.84 ± 0.34 (1313.1 ± 358.7) n = 8 (n = 9) | 2.61 ± 0.24 (1177.2 ± 210.2) n = 8 (n = 9) |
| Day 14 | 3.58 ± 0.51 (1888.5 ± 544.1) n = 8 (n = 9) | 3.06 ± 0.28 (1482.0 ± 298.5) n = 8 (n = 9) |

Nude mice bearing CFPAC tumors were treated with neutralizing antibody (100 μg each Ab/100 μl, intratumorally and peritumorally qd on Days 1, 3, 5, 8, 10, 12), or normal rabbit IgG in sterile PBS (400 μg/100 μl intratumorally and peritumorally qd on Days 1, 3, 5, 8, 10 and 12). Tumor volumes were determined every 3–4 days. Values are Mean±SE of relative tumor volume. Values in parentheses are Mean±SE actual tumor volume ($mm^3$).

TABLE 4

Effect of Neurotrophin Neutralizing Antibodies on the Body Weights of Nude Mice Bearing CFPAC Xenografts

| Group | Neutralizing Antibody (100 μg each Ab/100 μl) | Normal Rabbit IgG (400 μg/100 μl) |
| --- | --- | --- |
| Day 1 | 22.6 ± 0.4 n = 9 | 22.4 ± 0.4 n = 9 |
| Day 4 | 23.3 ± 0.4 n = 9 | 24.2 ± 0.5 n = 9 |
| Day 8 | 25.1 ± 0.5 n = 9 | 25.6 ± 0.6 n = 9 |
| Day 10 | 25.5 ± 0.5 n = 9 | 25.8 ± 0.5 n = 9 |
| Day 14 | 25.9 ± 0.6 n = 9 | 26.6 ± 0.4 n = 9 |

Nude mice bearing CFPAC tumors were treated with neutralizing antibody (100 μg each Ab/100 μl, intratumorally and peritumorally qd on Days 1, 3, 5, 8, 10, 12) or normal rabbit IgG in sterile PBS (400 μg/100 μl intratumorally and peritumorally qd on Days 1, 3, 5, 8, 10 and 12). Body weights were determined every 3–4 days. Values are Mean±SE of body weights (g).

Example 7

Individual Calculated Tumor Volumes and Body Weight

Exponentially growing cells, which were cultured as described above, were harvested and injected (5×10⁶ cells/mouse) into the right flank of nude mice. Animals bearing tumors of 100–500 $mm^3$ size were randomized into the appropriate groups and dosing with using a cocktail of neurotrophin (anti-NGF, anti-BDNF, anti-NT-3, and anti-NT-4/5) neutralizing antibodies (100 μg of each antibody in a total volume of 100 μl, 50 μl intratumorally and 50 μl peritumorally) or normal rabbit IgG (400 μg/100 μl, 50 μl intratumorally and 50 μl peritumorally). The mice received injections of antibodies once a day, three days per week on Days 1, 3, 5, 8, 10, and 12.

Tumors were measured every 2–3 days using a vernier caliper. Tumor volumes, mean tumor volumes and standard errors were also calculated as described above. Relative tumor volumes were determined at every data point using the following formula: mean $v_t$/mean $v_o$ where $v_t$ refers to tumor volume at a given day and $v_o$ refers to tumor volume at the initiation of dosing (Day 1). Any mouse with a tumor volume on the final day of analysis that deviated from the mean tumor volume on the final day of analysis by more than two standard deviations was removed from the analyses at every data point. Statistical analyses were calculated as described above with $p \leq 0.05$ deemed significant.

| | | | Effects of Neurotrophin Neutralizing Antibodies on ASPC1 Xenografts | | | |
|---|---|---|---|---|---|---|
| Treatment | cage # | Mouse # | Day 1 Length | width | V (mm3) | Fold |
| Neut. Ab | 1 | R-1 | 7.60 | 9.80 | 339.28 | 1.00 |
| 100 ug/100 ul | | L-1 | 6.60 | 8.10 | 205.74 | 1.00 |
| it, pt | | R-2 | 7.40 | 5.90 | 152.02 | 1.00 |
| | | L-2 | 8.80 | 7.60 | 287.15 | 1.00 |
| N = 10 | | Un | 5.80 | 7.20 | 142.13 | 1.00 |
| | 2 | R-1 | 6.60 | 7.60 | 186.47 | 1.00 |
| | | L-1 | 7.40 | 8.60 | 266.58 | 1.00 |
| | | R-2 | 5.60 | 8.10 | 162.69 | 1.00 |
| | | L-2 | 7.20 | 6.00 | 149.29 | 1.00 |
| | | Un | 6.60 | 8.80 | 234.16 | 1.00 |
| Average | | | | | 212.60 | 1.00 |
| Std. Err. | | | | | 21.30 | 0.00 |
| IgG | 3 | R-1 | 7.70 | 7.10 | 211.83 | 1.00 |
| 100 ug/100 ul | | L-1 | 7.60 | 8.30 | 262.58 | 1.00 |
| it, pt | | R-2 | 7.10 | 7.30 | 195.39 | 1.00 |
| | | L-2 | 6.00 | 6.80 | 136.72 | 1.00 |
| N = 10 | | Un | 7.60 | 6.60 | 186.47 | 1.00 |
| | 4 | R-1 | 5.70 | 7.40 | 144.66 | 1.00 |
| | | L-1 | 8.30 | 7.70 | 267.71 | 1.00 |
| | | R-2 | 7.00 | 7.50 | 199.30 | 1.00 |
| | | L-2 | 6.00 | 6.40 | 124.66 | 1.00 |
| | | Un | 8.00 | 8.80 | 309.64 | 1.00 |
| Average | | | | | 203.90 | 1.00 |
| Std. Err. | | | | | 19.30 | 0.00 |
| Treatment | cage # | Mouse # | Day 3 Length | width | V (mm3) | Fold |
| Neut. Ab | 1 | R-1 | 7.00 | 8.00 | 219.91 | 0.65 |
| 100 ug/100 ul | | L-1 | 8.90 | 8.00 | 315.02 | 1.53 |
| it, pt | | R-2 | 8.80 | 6.10 | 209.40 | 1.38 |
| | | L-2 | 9.20 | 7.90 | 325.37 | 1.13 |
| N = 10 | | Un | 6.80 | 10.00 | 299.08 | 2.10 |
| | 2 | R-1 | 5.90 | 7.40 | 152.02 | 0.82 |
| | | L-1 | 6.00 | 8.00 | 175.93 | 0.66 |
| | | R-2 | 9.60 | 7.20 | 304.01 | 1.87 |
| | | L-2 | 5.00 | 6.50 | 97.85 | 0.66 |
| | | Un | 5.70 | 7.80 | 157.13 | 0.67 |
| Average | | | | | 225.50 | 1.14 |
| Std. Err. | | | | | 25.50 | 0.17 |
| IgG | 3 | R-1 | 9.00 | 7.40 | 285.95 | 1.35 |
| 100 ug/100 ul | | L-1 | 6.90 | 7.80 | 207.12 | 0.79 |
| it, pt | | R-2 | 7.00 | 8.30 | 232.72 | 1.19 |
| | | L-2 | 6.70 | 7.00 | 168.21 | 1.23 |
| N = 10 | | Un | 9.80 | 6.00 | 243.22 | 1.30 |
| | 4 | R-1 | 10.00 | 6.80 | 299.08 | 2.07 |
| | | L-1 | 11.60 | 9.60 | 618.07 | 2.31 |
| | | R-2 | 6.50 | 8.00 | 197.40 | 0.99 |
| | | L-2 | 6.35 | 7.90 | 187.15 | 1.50 |
| | | Un | 9.60 | 7.50 | 322.33 | 1.04 |
| Average | | | | | 276.12 | 1.37 |
| Std. Err. | | | | | 41.25 | 0.15 |
| Treatment | cage # | Mouse # | Day 5 Length | width | V (mm3) | Fold |
| Neut. Ab | 1 | R-1 | 6.90 | 7.00 | 175.76 | 0.52 |
| 100 ug/100 ul | | L-1 | 8.90 | 7.00 | 259.33 | 1.26 |
| it, pt | | R-2 | 8.50 | 6.20 | 202.81 | 1.33 |
| | | L-2 | 6.60 | 7.80 | 194.08 | 0.68 |
| N = 10 | | Un | 7.90 | 11.00 | 429.98 | 3.03 |
| | 2 | R-1 | 5.60 | 6.60 | 118.05 | 0.63 |
| | | L-1 | 6.80 | 7.00 | 171.97 | 0.65 |
| | | R-2 | 8.00 | 7.60 | 248.31 | 1.53 |
| | | L-2 | 7.40 | 6.00 | 155.76 | 1.04 |
| | | Un | 6.00 | 6.60 | 130.63 | 0.56 |
| Average | | | | | 208.66 | 1.12 |

-continued

|  |  |  |  |  | 28.40 | 0.24 |
|---|---|---|---|---|---|---|
| IgG | 3 | R-1 | 7.50 | 8.80 | 281.64 | 1.33 |
| 100 ug/100 ul |  | L-1 | 8.90 | 6.90 | 254.02 | 0.97 |
| it, pt |  | R-2 | 7.90 | 9.50 | 341.88 | 1.75 |
|  |  | L-2 | 9.50 | 6.20 | 242.09 | 1.77 |
| N = 10 |  | Un | 10.00 | 6.00 | 251.33 | 1.35 |
|  | 4 | R-1 | 9.60 | 7.50 | 322.33 | 2.23 |
|  |  | L-1 | 10.50 | 11.60 | 704.71 | 2.63 |
|  |  | R-2 | 8.80 | 7.00 | 254.80 | 1.28 |
|  |  | L-2 | 9.50 | 7.00 | 287.26 | 2.30 |
|  |  | Un | 9.90 | 9.30 | 462.80 | 1.49 |
| Average |  |  |  |  | 340.28 | 1.71 |
| Std. Err. |  |  |  |  | 45.54 | 0.16 |

| Treatment | cage # | Mouse # | Day 8 Length | width | V (mm3) | Fold |
|---|---|---|---|---|---|---|
| Neut. Ab | 1 | R-1 | 8.00 | 6.60 | 201.82 | 0.59 |
| 100 ug/100 ul |  | L-1 | 8.80 | 8.00 | 309.64 | 1.50 |
| it, pt |  | R-2 | 8.80 | 7.00 | 254.80 | 1.68 |
|  |  | L-2 | 7.20 | 7.60 | 212.02 | 0.74 |
| N = 10 |  | Un | 6.70 | 11.00 | 341.52 | 2.40 |
|  | 2 | R-1 | 6.00 | 7.90 | 172.49 | 0.93 |
|  |  | L-1 | 5.80 | 6.60 | 124.27 | 0.47 |
|  |  | R-2 | 6.00 | 8.00 | 175.93 | 1.08 |
|  |  | L-2 | 8.50 | 8.80 | 338.78 | 2.27 |
|  |  | Un | 6.60 | 6.80 | 157.44 | 0.67 |
| Average |  |  |  |  | 228.87 | 1.23 |
| Std. Err. |  |  |  |  | 24.70 | 0.22 |
| IgG | 3 | R-1 | 8.50 | 8.80 | 338.78 | 1.60 |
| 100 ug/100 ul |  | L-1 | 6.90 | 8.80 | 249.57 | 0.95 |
| it, Pt |  | R-2 | 10.00 | 9.20 | 462.44 | 2.37 |
|  |  | L-2 | 10.40 | 6.90 | 325.01 | 2.38 |
| N = 10 |  | Un | 11.40 | 6.00 | 311.58 | 1.67 |
|  | 4 | R-1 | 10.90 | 6.35 | 312.58 | 2.16 |
|  |  | L-1 | 11.00 | 11.80 | 774.78 | 2.89 |
|  |  | R-2 | 8.80 | 6.90 | 249.57 | 1.25 |
|  |  | L-2 | 9.50 | 7.00 | 287.26 | 2.30 |
|  |  | Un | 10.40 | 9.30 | 498.83 | 1.61 |
| Average |  |  |  |  | 381.04 | 1.92 |
| Std. Err. |  |  |  |  | 50.90 | 0.18 |

| Treatment | cage # | Mouse # | Day 10 Length | width | V (mm3) | Fold |
|---|---|---|---|---|---|---|
| Neut. Ab | 1 | R-1 | 6.30 | 7.00 | 153.55 | 0.45 |
| 100 ug/100 ul |  | L-1 | 8.00 | 7.40 | 238.68 | 1.16 |
| it, pt |  | R-2 | 9.60 | 10.00 | 492.60 | 3.24 |
|  |  | L-2 | 6.30 | 6.60 | 140.42 | 0.49 |
| N = 10 |  | Un | 8.00 | 10.00 | 376.99 | 2.65 |
|  | 2 | R-1 | 6.00 | 6.35 | 123.19 | 0.66 |
|  |  | L-1 | 5.00 | 6.20 | 90.90 | 0.34 |
|  |  | R-2 | 6.20 | 6.80 | 143.49 | 0.88 |
|  |  | L-2 | 5.50 | 7.40 | 137.45 | 0.92 |
|  |  | Un | 5.00 | 6.70 | 102.61 | 0.44 |
| Average |  |  |  |  | 199.90 | 1.12 |
| Std. Err. |  |  |  |  | 41.90 | 0.31 |
| IgG | 3 | R-1 | 10.00 | 8.00 | 376.99 | 1.78 |
| 100 ug/100 ul |  | L-1 | 7.90 | 6.20 | 180.80 | 0.69 |
| it, pt |  | R-2 | 11.00 | 8.80 | 501.78 | 2.57 |
|  |  | L-2 | 11.75 | 7.80 | 469.08 | 3.43 |
| N = 10 |  | Un | 11.20 | 8.00 | 450.38 | 2.42 |
|  | 4 | R-1 | 11.00 | 8.00 | 437.73 | 3.03 |
|  |  | L-1 | 11.90 | 10.90 | 774.24 | 2.89 |
|  |  | R-2 | 9.40 | 7.00 | 282.51 | 1.42 |
|  |  | L-2 | 9.00 | 8.00 | 320.44 | 2.57 |
|  |  | Un | 10.50 | 9.60 | 530.43 | 1.71 |
| Average |  |  |  |  | 432.43 | 2.25 |
| Std. Err. |  |  |  |  | 51.00 | 0.26 |

| Treatment | cage # | Mouse # | Day 12 Length | width | V (mm3) | Fold |
|---|---|---|---|---|---|---|
| Neut. Ab | 1 | R-1 | 6.60 | 7.70 | 190.26 | 0.56 |
| 100 ug/100 ul |  | L-1 | 9.80 | 8.60 | 405.99 | 1.97 |
| it, pt |  | R-2 | 10.70 | 11.00 | 668.66 | 4.40 |
|  |  | L-2 | 5.30 | 7.20 | 124.88 | 0.43 |
| N = 10 |  | Un | 7.00 | 11.00 | 362.85 | 2.55 |
|  | 2 | R-1 | 6.00 | 7.90 | 172.49 | 0.93 |

-continued

| Treatment | cage # | Mouse # | Length | width | V (mm3) | Fold |
|---|---|---|---|---|---|---|
| | | L-1 | 5.50 | 5.00 | 75.59 | 0.28 |
| | | R-2 | 6.00 | 6.80 | 136.72 | 0.84 |
| | | L-2 | 6.00 | 7.40 | 155.76 | 1.04 |
| | | Un | 5.00 | 6.40 | 95.50 | 0.41 |
| Average | | | | | 238.80 | 1.34 |
| Std. Err. | | | | | 58.91 | 0.41 |
| IgG | 3 | R-1 | 8.80 | 10.00 | 433.12 | 2.04 |
| 100 ug/100 ul | | L-1 | 8.80 | 6.50 | 229.12 | 0.87 |
| it, pt | | R-2 | 12.70 | 10.00 | 754.74 | 3.86 |
| | | L-2 | 7.80 | 11.80 | 472.28 | 3.45 |
| N = 10 | | Un | 11.20 | 8.80 | 516.06 | 2.77 |
| | 4 | R-1 | 11.00 | 8.00 | 437.73 | 3.03 |
| | | L-1 | 12.20 | 12.20 | 950.78 | 3.55 |
| | | R-2 | 8.00 | 10.00 | 376.99 | 1.89 |
| | | L-2 | 12.00 | 8.00 | 502.66 | 4.03 |
| | | Un | 11.00 | 9.20 | 535.18 | 1.73 |
| Average | | | | | 520.86 | 2.72 |
| Std. Err. | | | | | 63.49 | 0.33 |

| Treatment | cage # | Mouse # | Day 15 Length | width | V (mm3) | Fold |
|---|---|---|---|---|---|---|
| Neut. Ab | 1 | R-1 | 7.50 | 9.30 | 306.78 | 0.90 |
| 100 ug/100 ul | | L-1 | 10.00 | 8.40 | 404.64 | 1.97 |
| it, pt | | R-2 | 9.40 | 12.00 | 631.96 | 4.16 |
| | | L-2 | 7.30 | 6.85 | 185.24 | 0.65 |
| N = 10 | | Un | 9.60 | 12.00 | 651.44 | 4.58 |
| | 2 | R-1 | 6.50 | 8.40 | 212.98 | 1.14 |
| | | L-1 | 5.00 | 5.30 | 71.46 | 0.27 |
| | | R-2 | 7.80 | 6.40 | 185.58 | 1.14 |
| | | L-2 | 6.80 | 7.40 | 187.07 | 1.25 |
| | | Un | 5.50 | 7.00 | 125.99 | 0.54 |
| Average | | | | | 296.31 | 1.66 |
| Std. Err. | | | | | 64.40 | 0.47 |
| IgG | 3 | R-1 | 10.20 | 8.90 | 453.9345 | 2.14 |
| 100 ug/100 ul | | L-1 | 6.80 | 9.40 | 271.0949 | 1.03 |
| it, pt | | R-2 | 11.60 | 12.90 | 959.8059 | 4.91 |
| | | L-2 | 12.90 | 12.30 | 1046.803 | 7.66 |
| N = 10 | | Un | 12.70 | 9.00 | 649.3452 | 3.48 |
| | 4 | R-1 | 11.30 | 8.30 | 481.2628 | 3.33 |
| | | L-1 | 12.60 | 12.80 | 1072.467 | 4.01 |
| | | R-2 | 10.00 | 8.40 | 404.6381 | 2.03 |
| | | L-2 | 12.00 | 8.40 | 538.3446 | 4.32 |
| | | Un | 11.10 | 11.10 | 716.0916 | 2.31 |
| Average | | | | | 659.38 | 3.52 |
| Std. Err. | | | | | 89.35 | 0.59 |

Effects of Neutralizing Antibodies on the Body Weights of Nude Mice Bearing AsPC-1 Xenografts

| Treatment | cage # | Mouse # | Day 1 Weight (g) | Day 3 | Day 5 | Day 8 | Day 10 | Day 12 | Day 15 |
|---|---|---|---|---|---|---|---|---|---|
| Neut. Ab | 1 | R-1 | 22.20 | 22.90 | 22.70 | 22.60 | 23.20 | 23.60 | 25.70 |
| 400 ug/100 ul | | L-1 | 24.70 | 24.70 | 24.00 | 24.20 | 24.20 | 23.10 | 25.50 |
| it, pt | | R-2 | 23.00 | 21.90 | 21.90 | 21.70 | 21.60 | 21.90 | 22.00 |
| | | L-2 | 24.20 | 24.50 | 24.70 | 24.90 | 24.20 | 24.40 | 23.70 |
| | | Un | 22.50 | 22.10 | 22.70 | 21.90 | 21.40 | 21.20 | 22.30 |
| N = 10 | 2 | R-1 | 25.20 | 23.00 | 23.00 | 22.80 | 24.10 | 24.30 | 26.10 |
| | | L-1 | 22.30 | 21.50 | 22.30 | 22.40 | 21.80 | 22.10 | 23.30 |
| | | R-2 | 23.10 | 24.10 | 24.20 | 22.40 | 22.50 | 22.10 | 25.50 |
| | | L-2 | 22.40 | 23.10 | 23.50 | 23.10 | 22.80 | 21.80 | 26.10 |
| | | Un | 21.50 | 21.10 | 20.10 | 23.10 | 24.10 | 23.40 | 23.80 |
| Average | | | 23.10 | 22.90 | 22.90 | 22.90 | 23.00 | 22.80 | 24.40 |
| Std. Err. | | | 0.30 | 0.30 | 0.40 | 0.30 | 0.30 | 0.30 | 0.40 |
| IgG | 3 | R-1 | 24.70 | 21.60 | 25.10 | 28.00 | 23.40 | 23.60 | 26.10 |
| 400 ug/100 ul | | L-1 | 21.50 | 21.20 | 22.50 | 23.10 | 24.10 | 22.40 | 23.60 |
| it, pt | | R-2 | 22.90 | 22.10 | 22.80 | 23.00 | 22.90 | 23.70 | 24.30 |
| | | L-2 | 21.80 | 21.30 | 23.10 | 21.00 | 23.10 | 22.30 | 25.60 |
| N = 10 | | Un | 24.00 | 21.40 | 23.50 | 23.20 | 22.30 | 25.10 | 22.10 |
| | 4 | R-1 | 22.80 | 22.10 | 22.20 | 23.40 | 22.00 | 23.70 | 22.80 |
| | | L-1 | 22.80 | 21.00 | 22.70 | 24.10 | 21.50 | 20.60 | 22.60 |
| | | R-2 | 23.70 | 24.00 | 24.20 | 22.60 | 23.30 | 23.40 | 25.10 |
| | | L-2 | 25.10 | 23.60 | 23.60 | 21.90 | 22.70 | 23.60 | 24.20 |
| | | Un | 23.60 | 23.00 | 25.00 | 23.40 | 23.60 | 25.00 | 26.30 |
| Average | | | 23.30 | 22.10 | 23.50 | 23.40 | 22.90 | 23.30 | 24.30 |
| Std. Err. | | | 0.30 | 0.30 | 0.30 | 0.50 | 0.20 | 0.40 | 0.40 |

-continued

Effects of Neurotrophin Neutralizing Antibodies on CFPAC Xenografts in Nude Mice

| Treatment | cage # | Mouse # | Day 1 Length | width | V (mm3) | Fold |
|---|---|---|---|---|---|---|
| Neut. Ab | 1 | R-1 | 9.60 | 13.60 | 792.99 | 1.00 |
| 100 ug/100 ul | | L-1 | 7.00 | 6.90 | 175.76 | 1.00 |
| it, pt | | R-2 | 8.30 | 10.00 | 397.65 | 1.00 |
| | | L-2 | 8.10 | 8.50 | 299.21 | 1.00 |
| N = 9 | | 0 | 8.60 | 8.80 | 344.75 | 1.00 |
| | 2 | R-1 | 8.10 | 12.30 | 532.10 | 1.00 |
| | | L-1 | 7.20 | 6.00 | 149.29 | 1.00 |
| | | R-2 | 10.30 | 13.90 | 907.06 | 1.00 |
| | | 0 | 9.10 | 7.20 | 279.60 | 1.00 |
| Average | | | | | 430.90 | 1.00 |
| Std. Err. | | | | | 88.30 | 0.00 |
| IgG | 3 | R-1 | 7.00 | 9.00 | 263.89 | 1.00 |
| 400 ug/100 ul | | L-1 | 8.30 | 10.40 | 422.59 | 1.00 |
| it, pt | | R-2 | 7.70 | 6.40 | 181.91 | 1.00 |
| | | L-2 | 9.50 | 13.00 | 727.48 | 1.00 |
| N = 9 | 4 | 0 | 10.50 | 13.00 | 839.79 | 1.00 |
| | | R-1 | 7.00 | 9.00 | 263.89 | 1.00 |
| | | L-1 | 9.00 | 6.30 | 227.11 | 1.00 |
| | | R-2 | 8.80 | 7.90 | 303.95 | 1.00 |
| | | 0 | 8.50 | 13.30 | 645.20 | 1.00 |
| Average | | | | | 430.60 | 1.00 |
| Std. Err. | | | | | 81.40 | 1.00 |

| Treatment | cage # | Mouse # | Day 4 Length | width | V (mm3) | Fold |
|---|---|---|---|---|---|---|
| Neut. Ab | 1 | R-1 | 11.30 | 15.50 | 1228.89 | 1.55 |
| 100 ug/100 ul | | L-1 | 6.90 | 7.00 | 175.76 | 1.00 |
| it, pt | | R-2 | 10.00 | 9.70 | 500.27 | 1.26 |
| | | L-2 | 8.80 | 9.90 | 426.51 | 1.43 |
| N = 9 | | 0 | 7.60 | 9.40 | 317.95 | 0.92 |
| | 2 | R-1 | 9.40 | 12.20 | 648.50 | 1.22 |
| | | R-2 | 7.80 | 8.40 | 277.88 | 1.86 |
| | | R-2 | 12.80 | 14.40 | 1312.54 | 1.45 |
| | | 0 | 8.90 | 9.40 | 400.81 | 1.43 |
| Average | | | | | 587.60 | 1.35 |
| Std. Err. | | | | | 136.70 | 0.09 |
| IgG | 3 | R-1 | 7.20 | 10.00 | 324.21 | 1.23 |
| 400 ug/100 ul | | L-1 | 9.90 | 10.00 | 515.77 | 1.22 |
| it, pt | | R-2 | 8.60 | 7.30 | 261.33 | 1.44 |
| | | L-2 | 9.90 | 13.30 | 799.73 | 1.10 |
| N = 9 | | 0 | 10.50 | 15.30 | 1085.10 | 1.29 |
| | 4 | R-1 | 8.80 | 10.00 | 433.12 | 1.64 |
| | | L-1 | 9.60 | 6.00 | 235.24 | 1.04 |
| | | R-2 | 9.80 | 9.90 | 500.38 | 1.65 |
| | | 0 | 8.50 | 13.00 | 621.97 | 0.96 |
| Average | | | | | 530.70 | 1.29 |
| Std. Err. | | | | | 91.30 | 0.08 |

| Treatment | cage # | Mouse # | Day 8 Length | width | V (mm3) | Fold |
|---|---|---|---|---|---|---|
| Neut. Ab | 1 | R-1 | 13.00 | 21.50 | 2524.47 | 3.18 |
| 100 ug/100 ul | | L-1 | 6.85 | 11.10 | 357.31 | 2.03 |
| it, pt | | R-2 | 11.90 | 14.00 | 1129.65 | 2.84 |
| | | L-2 | 10.20 | 11.10 | 631.35 | 2.11 |
| N = 9 | | 0 | 8.70 | 8.80 | 350.76 | 1.02 |
| | 2 | R-1 | 9.80 | 13.50 | 807.02 | 1.52 |
| | | L-1 | 8.10 | 9.10 | 331.91 | 2.22 |
| | | R-2 | 14.40 | 14.10 | 1514.94 | 1.67 |
| | | 0 | 9.00 | 10.00 | 447.68 | 1.60 |
| Average | | | | | 899.45 | 2.02 |
| Std. Err. | | | | | 243.60 | 0.22 |
| IgG | 3 | R-1 | 7.90 | 10.75 | 414.65 | 1.57 |
| 400 ug/100 ul | | L-1 | 11.80 | 13.10 | 1007.68 | 2.38 |
| it, pt | | R-2 | 8.90 | 9.90 | 433.66 | 2.38 |
| | | L-2 | 11.90 | 15.00 | 1257.07 | 1.73 |
| N = 9 | | 0 | 12.40 | 14.80 | 1306.84 | 1.56 |
| | 4 | R-1 | 10.70 | 12.20 | 782.616 | 2.97 |
| | | L-1 | 8.00 | 10.75 | 422.153 | 1.86 |
| | | R-2 | 8.80 | 9.40 | 394.141 | 1.30 |
| | | 0 | 11.70 | 18.00 | 1637.51 | 2.54 |
| Average | | | | | 850.7 | 2.03 |

-continued

| | | | | | | |
|---|---|---|---|---|---|---|
| Std. Err. | | | | | 157.1 | 0.19 |

| Treatment | cage # | Mouse # | Day 10 Length | width | V (mm3) | Fold |
|---|---|---|---|---|---|---|
| Neut. Ab | 1 | R-1 | 14.00 | 23.00 | 3119.1 | 3.93 |
| 100 ug/100 ul | | L-1 | 11.60 | 8.00 | 476.18 | 2.71 |
| it, pt | | R-2 | 12.00 | 14.40 | 1194.3 | 3.00 |
| | | L-2 | 11.50 | 12.60 | 914.23 | 3.06 |
| N = 9 | | 0 | 8.00 | 10.50 | 406.84 | 1.18 |
| | 2 | R-1 | 10.20 | 13.80 | 884.42 | 1.66 |
| | | L-1 | 10.30 | 10.00 | 547.4 | 3.67 |
| | | R-2 | 16.60 | 20.00 | 3181.2 | 3.51 |
| | | 0 | 15.00 | 10.80 | 1094.2 | 3.91 |
| Average | | | | | 1313 | 2.96 |
| Std. Err. | | | | | 358.7 | 0.325 |
| IgG | 3 | R-1 | 10.50 | 8.60 | 451.53 | 1.71 |
| 400 ug/100 ul | | L-1 | 14.50 | 14.60 | 1612.8 | 3.82 |
| it, pt | | R-2 | 12.60 | 7.70 | 515.62 | 2.83 |
| | | L-2 | 17.60 | 11.10 | 1467.9 | 2.02 |
| N = 9 | | 0 | 12.70 | 19.40 | 2070.5 | 2.47 |
| | 4 | R-1 | 12.40 | 10.80 | 813.4 | 3.08 |
| | | L-1 | 8.00 | 11.40 | 463.2 | 2.04 |
| | | R-2 | 13.30 | 14.00 | 1330.8 | 4.38 |
| | | 0 | 11.80 | 19.40 | 1869.9 | 2.90 |
| Average | | | | | 1177 | 2.81 |
| Std. Err. | | | | | 210.2 | 0.29 |

| Treatment | cage # | Mouse # | Day 14 Length | width | V (mm3) | Fold |
|---|---|---|---|---|---|---|
| Neut. Ab | 1 | R-1 | 15.50 | 25.60 | 4269.6 | 5.38 |
| 100 ug/100 ul | | L-1 | 12.10 | 8.55 | 559.3 | 3.18 |
| it, pt | | R-2 | 14.90 | 12.70 | 1367.3 | 3.44 |
| | | L-2 | 12.60 | 14.00 | 1228.4 | 4.11 |
| N = 9 | | 0 | 10.80 | 8.00 | 425.25 | 1.23 |
| | 2 | R-1 | 14.90 | 10.20 | 998.69 | 1.88 |
| | | L-1 | 11.00 | 10.30 | 631.8 | 4.23 |
| | | R-2 | 18.90 | 22.70 | 4672.5 | 5.15 |
| | | 0 | 15.70 | 19.60 | 2843.8 | 10.17 |
| Average | | | | | 1889 | 4.31 |
| Std. Err. | | | | | 544.1 | 0.86 |
| IgG | 3 | R-1 | 8.60 | 10.80 | 471.73 | 1.79 |
| 400 ug/100 ul | | L-1 | 14.80 | 15.30 | 1784.4 | 4.22 |
| it, pt | | R-2 | 11.10 | 8.70 | 500.58 | 2.75 |
| | | L-2 | 12.20 | 17.20 | 1615.1 | 2.22 |
| N = 9 | | 0 | 15.00 | 21.00 | 2968.8 | 3.54 |
| | 4 | R-1 | 13.30 | 11.00 | 930.72 | 3.53 |
| | | L-1 | 12.60 | 9.00 | 641.26 | 2.82 |
| | | R-2 | 14.10 | 17.70 | 2077.7 | 6.84 |
| | | 0 | 12.40 | 21.40 | 2348.1 | 3.64 |
| Average | | | | | 1482 | 3.48 |
| Std. Err. | | | | | 298.6 | 0.49 |

Effects of Neutralizing Antibodies on the Body Weights of Nude Mice Bearing CFPAC Xenografts

| Treatment | cage # | Mouse # | Day 1 Weight (g) | Day 4 | Day 8 | Day 10 | Day 14 |
|---|---|---|---|---|---|---|---|
| Neut. Ab | 1 | R-1 | 23.70 | 23.90 | 26.00 | 26.50 | 28.00 |
| 100 ug/100 ul | | L-1 | 21.80 | 21.90 | 23.70 | 23.50 | 23.70 |
| it, pt | | R-2 | 23.60 | 23.30 | 24.60 | 25.50 | 26.10 |
| | | L-2 | 21.10 | 21.90 | 24.00 | 24.50 | 24.60 |
| | | Un | 23.80 | 23.50 | 25.20 | 26.00 | 26.10 |
| N = 10 | 2 | R-1 | 23.60 | 25.80 | 27.40 | 26.00 | 27.90 |
| | | L-1 | 20.50 | 21.70 | 23.30 | 23.70 | 26.90 |
| | | R-2 | 22.50 | 24.20 | 26.40 | 28.50 | 23.80 |
| | | Un | 25.20 | 22.30 | 29.90 | 33.40 | 32.80 |
| Average | | | 22.60 | 23.30 | 25.10 | 25.50 | 25.90 |
| Std. Err. | | | 0.46 | 0.49 | 0.50 | 0.57 | 0.60 |
| IgG | 3 | R-1 | 21.50 | 22.40 | 24.30 | 24.10 | 25.40 |
| 100 ug/100 ul | | L-1 | 21.90 | 23.50 | 25.00 | 25.80 | 27.10 |
| it, pt | | R-2 | 24.30 | 26.90 | 28.10 | 27.70 | 27.80 |
| | | L-2 | 23.80 | 25.10 | 27.10 | 27.20 | 27.90 |
| N = 10 | | Un | 23.00 | 24.40 | 25.90 | 25.90 | 26.20 |
| | 4 | R-1 | 22.90 | 25.20 | 26.70 | 27.60 | 27.40 |
| | | L-1 | 20.10 | 22.40 | 22.50 | 23.20 | 24.40 |
| | | R-2 | 21.90 | 25.50 | 22.70 | 26.00 | 28.60 |

| | | -continued | | | | |
|---|---|---|---|---|---|---|
| | Un | 21.80 | 24.00 | 25.30 | 24.60 | 26.20 |
| Average | | 22.40 | 24.20 | 25.60 | 25.80 | 26.60 |
| Std. Err. | | 0.48 | 0.53 | 0.62 | 0.59 | 0.43 |

What is claimed is:

1. A method of treating cancer comprising administering to a mammal a therapeutically effective amount of at least one anti-neurotrophin antibody, wherein said cancer is a neoplasm that expresses neurotrophin receptors.

2. A method of treating cancer comprising administering to a mammal a therapeutically effective amount of at least one anti-neurotrophin antibody, wherein said cancer is prostate or pancreatic cancer.

3. The method of claim 1 wherein said neurotrophin is NGF, BDNF, NT-3, NT-4/5, NT-6, or NT-7.

4. The method of claim 1 wherein said antibody is a humanized antibody, chimeric antibody, F(ab) fragment, or F(ab)$_2$ fragment.

5. The method of claim 1 wherein said antibody is a monoclonal antibody.

6. The method of claim 1 wherein said mammal is a human.

7. A method of treating prostate or pancreatic tumors comprising contacting said tumor with a therapeutically effective amount of at least one neutralizing neurotrophin antibody, wherein said neurotrophin is selected from the group consisting of NGF, BDNF, NT-3, NT-4/5, NT-6, and NT-7.

8. A method of reducing prostatic or pancreatic tumor volume comprising contacting said tumor with at least one anti-neurotrophin antibody.

9. The method of claim 8 wherein said neurotrophin is NGF, BDNF, NT-3, NT-4/5, NT-6, or NT-7.

10. The method of claim 8 said antibody is a humanized antibody, chimeric antibody, F(ab) fragment, or F(ab)$_2$ fragment.

11. The method of claim 8 wherein said antibody is a monoclonal antibody.

12. A method of reducing prostatic or pancreatic tumor growth rate comprising contacting said tumor with at least one anti-neurotrophin antibody.

13. The method of claim 12 wherein said neurotrophin is NGF, BDNF, NT-3, NT-4/5, NT-6, or NT-7.

14. The method of claim 12 wherein said antibody is a humanized antibody, chimeric antibody, F(ab) fragment, or F(ab)$_2$ fragment.

15. The method of claim 12 wherein said antibody is a monoclonal antibody.

* * * * *

UNITED STATES PATENT AND TRADEMARK OFFICE
CERTIFICATE OF CORRECTION

PATENT NO.     : 6,548,062 B2
DATED          : April 15, 2003
INVENTOR(S)    : Buchkovich et al.

It is certified that error appears in the above-identified patent and that said Letters Patent is hereby corrected as shown below:

Column 4,
Line 6, please delete the first occurrence of "are".

Column 5,
Line 59, please delete "know" and insert -- known --; and please delete "a".

Column 18,
Line 22, please delete "form" and insert --from -- therefor.

Column 32,
Line 14, following "claim 8", please insert -- wherein --.

Signed and Sealed this

Twenty-first Day of June, 2005

JON W. DUDAS
*Director of the United States Patent and Trademark Office*